United States Patent
Jónsson et al.

(10) Patent No.: US 7,811,333 B2
(45) Date of Patent: Oct. 12, 2010

(54) SYSTEMS AND METHODS FOR PROCESSING LIMB MOTION

(75) Inventors: Helgi Jónsson, Reykjavík (IS); Arinbjörn Viggo Clausen, Reykjavík (IS); Heidrun G. Ragnarsdóttir, Reykjavík (IS)

(73) Assignee: Ossur hf, Reykjavik (IS)

( * ) Notice: Subject to any disclaimer, the term of this patent is extended or adjusted under 35 U.S.C. 154(b) by 1324 days.

(21) Appl. No.: 11/315,648

(22) Filed: Dec. 22, 2005

(65) Prior Publication Data

US 2006/0135883 A1    Jun. 22, 2006

Related U.S. Application Data

(60) Provisional application No. 60/638,802, filed on Dec. 22, 2004.

(51) Int. Cl.
A61F 2/48    (2006.01)
(52) U.S. Cl. .......................................... 623/24; 623/47
(58) Field of Classification Search ................... 623/24, 623/47
See application file for complete search history.

(56) References Cited

U.S. PATENT DOCUMENTS

| | | | |
|---|---|---|---|
| 2,568,051 A | 9/1951 | Catranis | |
| 2,619,652 A | 12/1952 | Vesper | |
| 2,859,451 A | 11/1958 | Mauch | |
| 3,316,558 A | 5/1967 | Mortensen | |
| 3,501,776 A | 3/1970 | Beeker et al. | |
| 3,791,375 A | 2/1974 | Pfeifer | |
| 3,820,168 A | 6/1974 | Horvath | |
| 3,995,324 A | 12/1976 | Burch | |
| 4,030,141 A | 6/1977 | Graupe | |
| 4,065,815 A | 1/1978 | Sen-Jung | |

(Continued)

FOREIGN PATENT DOCUMENTS

DE    42 29 330    3/1994

(Continued)

OTHER PUBLICATIONS

Au S K et al., "An EMG-Position Controlled System for an Active Ankle-Foot Prosthesis: An Initial Experimental Study" Rehabilitation Robotics, 2005. ICORR 2005., 9th International Conference in Chicago, IL, USA Jun. 28-Jul. 1, 2005, Piscataway, NJ, IEEE, Jun. 28, 2005, pp. 375-379, XP008078417.

(Continued)

*Primary Examiner*—Bruce E Snow
(74) *Attorney, Agent, or Firm*—Knobbe, Martens, Olson & Bear, LLP

(57) ABSTRACT

Control systems and methods are disclosed for processing a time series of signals associated with the movement of a device associated with a limb. The time series of motion signals is filtered, such as thorough an autoregressive filter, and compared to stored data sets representing a limb-motion event and/or phase. In certain examples, a plurality of accelerometers generate the time series of motion signals based at least on acceleration measurements in three orthogonal directions and/or planes. The acceleration measurements may relate to the movement of an artificial limb, such as a prosthetic or orthotic device. Upon determining an event and/or phase of limb motion, the control system may trigger an actuator to appropriately adjust one or more prosthetic or orthotic joints.

15 Claims, 8 Drawing Sheets

U.S. PATENT DOCUMENTS

| | | | |
|---|---|---|---|
| 4,179,759 A | 12/1979 | Smith | |
| 4,209,860 A | 7/1980 | Graupe | |
| 4,212,087 A | 7/1980 | Mortensen | |
| 4,387,472 A | 6/1983 | Wilson | |
| 4,441,644 A | 4/1984 | Farian | |
| 4,521,924 A | 6/1985 | Jacobsen et al. | |
| 4,558,704 A | 12/1985 | Petrofsky | |
| 4,569,352 A | 2/1986 | Petrofsky et al. | |
| 4,649,934 A | 3/1987 | Fraser et al. | |
| 4,711,242 A | 12/1987 | Petrofsky | |
| 4,730,625 A | 3/1988 | Fraser et al. | |
| 4,770,662 A | 9/1988 | Giampapa | |
| 4,776,852 A | 10/1988 | Rubic | |
| 4,814,661 A | 3/1989 | Ratzlaff et al. | |
| 4,854,428 A | 8/1989 | Horvath | |
| 4,876,944 A | 10/1989 | Wilson et al. | |
| 4,892,554 A | 1/1990 | Robinson | |
| 4,944,755 A | 7/1990 | Hennequin et al. | |
| 4,994,086 A | 2/1991 | Edwards | |
| 5,033,291 A | 7/1991 | Podoloff et al. | |
| 5,044,360 A | 9/1991 | Janke | |
| 5,062,856 A | 11/1991 | Sawamura et al. | |
| 5,062,857 A | 11/1991 | Berringer et al. | |
| 5,086,785 A | 2/1992 | Gentile et al. | |
| 5,092,902 A | 3/1992 | Adams et al. | |
| 5,112,296 A | 5/1992 | Beard et al. | |
| 5,112,356 A | 5/1992 | Harris et al. | |
| 5,133,773 A | 7/1992 | Sawamura et al. | |
| 5,133,774 A | 7/1992 | Sawamura et al. | |
| 5,139,525 A | 8/1992 | Kristinsson | |
| 5,153,496 A | 10/1992 | LaForge | |
| 5,181,931 A | 1/1993 | Van de Veen | |
| 5,201,772 A | 4/1993 | Maxwell | |
| 5,217,500 A | 6/1993 | Phillips | |
| 5,219,365 A | 6/1993 | Sabolich | |
| 5,252,102 A | 10/1993 | Singer et al. | |
| 5,253,656 A | 10/1993 | Rincoe et al. | |
| 5,323,650 A | 6/1994 | Fullen et al. | |
| 5,336,269 A | 8/1994 | Smits | |
| 5,357,696 A | 10/1994 | Gray et al. | |
| 5,376,133 A | 12/1994 | Gramnas | |
| 5,376,137 A | 12/1994 | Shorter et al. | |
| 5,383,939 A | 1/1995 | James | |
| 5,405,407 A | 4/1995 | Kodama et al. | |
| 5,405,409 A | 4/1995 | Knoth | |
| 5,405,410 A | 4/1995 | Arbogast et al. | |
| 5,405,510 A | 4/1995 | Betts | |
| 5,408,873 A | 4/1995 | Schmidt et al. | |
| 5,413,611 A | 5/1995 | Haslam, II et al. | |
| 5,422,558 A | 6/1995 | Stewart | |
| 5,443,521 A | 8/1995 | Knoth et al. | |
| 5,443,524 A | 8/1995 | Sawamura et al. | |
| 5,443,528 A | 8/1995 | Allen | |
| 5,472,412 A | 12/1995 | Knoth | |
| 5,476,441 A | 12/1995 | Durfee et al. | |
| 5,504,415 A | 4/1996 | Podrazhansky et al. | |
| 5,545,232 A | 8/1996 | van de Veen | |
| 5,545,233 A | 8/1996 | Fitzlaff | |
| 5,563,458 A | 10/1996 | Ericson | |
| 5,566,479 A | 10/1996 | Gray et al. | |
| 5,571,205 A | 11/1996 | James | |
| 5,571,212 A | 11/1996 | Cornelius | |
| 5,571,213 A | 11/1996 | Allen | |
| 5,583,476 A | 12/1996 | Langford et al. | |
| 5,586,557 A | 12/1996 | Nelson et al. | |
| 5,642,096 A | 6/1997 | Leyerer et al. | |
| 5,650,704 A | 7/1997 | Pratt et al. | |
| 5,656,915 A | 8/1997 | Eaves | |
| 5,662,693 A | 9/1997 | Johnson et al. | |
| 5,678,448 A | 10/1997 | Fullen et al. | |
| 5,695,527 A | 12/1997 | Allen | |
| 5,704,945 A | 1/1998 | Wagner et al. | |
| 5,704,946 A | 1/1998 | Greene | |
| 5,728,170 A | 3/1998 | Becker et al. | |
| 5,746,774 A | 5/1998 | Kramer et al. | |
| 5,779,735 A | 7/1998 | Molino | |
| 5,800,568 A | 9/1998 | Atkinson et al. | |
| 5,888,212 A | 3/1999 | Petrofsky et al. | |
| 5,888,213 A | 3/1999 | Sears et al. | |
| 5,888,246 A | 3/1999 | Gow | |
| 5,893,891 A | 4/1999 | Zahedi | |
| 5,895,430 A | 4/1999 | O'Connor | |
| 5,919,149 A | 7/1999 | Allum | |
| 5,929,332 A | 7/1999 | Brown | |
| 5,955,667 A | 9/1999 | Fyfe | |
| 5,957,981 A | 9/1999 | Gramnas | |
| 5,972,035 A | 10/1999 | Blatchford | |
| 5,982,156 A | 11/1999 | Weimer et al. | |
| 5,998,930 A | 12/1999 | Upadhyay et al. | |
| 6,006,412 A | 12/1999 | Bergmann et al. | |
| 6,007,582 A | 12/1999 | May | |
| 6,061,577 A | 5/2000 | Andrieu et al. | |
| 6,091,977 A | 7/2000 | Tarjan et al. | |
| 6,113,642 A | 9/2000 | Petrofsky et al. | |
| 6,129,766 A | 10/2000 | Johnson et al. | |
| 6,165,226 A | 12/2000 | Wagner | |
| 6,183,425 B1 | 2/2001 | Whalen et al. | |
| 6,187,051 B1 | 2/2001 | van de Veen | |
| 6,195,921 B1 | 3/2001 | Truong | |
| 6,206,932 B1 | 3/2001 | Johnson | |
| 6,206,934 B1 | 3/2001 | Phillips | |
| 6,241,775 B1 | 6/2001 | Blatchford | |
| 6,301,964 B1 | 10/2001 | Fyfe et al. | |
| 6,342,076 B1 | 1/2002 | Lundborg | |
| 6,350,286 B1 | 2/2002 | Atkinson et al. | |
| 6,361,570 B1 | 3/2002 | Gow | |
| 6,373,152 B1 | 4/2002 | Wang et al. | |
| 6,409,695 B1 | 6/2002 | Connelly | |
| 6,423,098 B1 | 7/2002 | Biedermann | |
| 6,425,925 B1 | 7/2002 | Grundei | |
| 6,430,843 B1 | 8/2002 | Potter et al. | |
| 6,436,149 B1 | 8/2002 | Rincoe | |
| 6,443,993 B1 | 9/2002 | Koniuk | |
| 6,451,481 B1 | 9/2002 | Lee et al. | |
| 6,494,039 B2 | 12/2002 | Pratt et al. | |
| 6,500,210 B1 | 12/2002 | Sabolich et al. | |
| 6,513,381 B2 | 2/2003 | Fyfe et al. | |
| 6,517,585 B1 | 2/2003 | Zahedi et al. | |
| 6,522,266 B1 | 2/2003 | Soehren et al. | |
| 6,537,322 B1 | 3/2003 | Johnson et al. | |
| 6,587,728 B2 | 7/2003 | Fang et al. | |
| 6,589,287 B2 | 7/2003 | Lundborg | |
| 6,602,295 B1 | 8/2003 | Doddroe et al. | |
| 6,610,101 B2 | 8/2003 | Herr et al. | |
| 6,663,673 B2 | 12/2003 | Christensen | |
| 6,671,531 B2 | 12/2003 | Al-Ali et al. | |
| 6,679,920 B2 | 1/2004 | Biedermann et al. | |
| 6,695,885 B2 | 2/2004 | Sfchulman et al. | |
| 6,719,806 B1 | 4/2004 | Zahedi et al. | |
| 6,740,123 B2 | 5/2004 | Davalli et al. | |
| 6,743,260 B2 | 6/2004 | Townsend et al. | |
| 6,755,870 B1 | 6/2004 | Biedermann et al. | |
| 6,764,520 B2 | 7/2004 | Deffenbaugh et al. | |
| 6,770,045 B2 | 8/2004 | Naft et al. | |
| 6,811,571 B1 | 11/2004 | Phillips | |
| 6,855,170 B2 | 2/2005 | Gramnas | |
| 6,876,135 B2 | 4/2005 | Pelrine | |
| 6,955,692 B2 | 10/2005 | Grundei | |
| 6,966,933 B2 | 11/2005 | Christensen | |
| 7,029,500 B2 | 4/2006 | Martin | |
| 7,063,727 B2 | 6/2006 | Van Phillips et al. | |
| 7,131,998 B2 | 11/2006 | Pasolini | |
| 7,164,967 B2 | 1/2007 | Etienne-Cummings et al. | |
| 7,410,338 B2 | 8/2008 | Schiele et al. | |

| | | | |
|---|---|---|---|
| 7,431,737 B2 | 10/2008 | Ragnarsdottir et al. | |
| 2002/0087216 A1 | 7/2002 | Atkinson et al. | |
| 2002/0161451 A1 | 10/2002 | Biedermann et al. | |
| 2002/0183803 A1 | 12/2002 | Fang et al. | |
| 2002/0198604 A1 | 12/2002 | Schulman et al. | |
| 2003/0029247 A1 | 2/2003 | Biedermann et al. | |
| 2003/0067245 A1 | 4/2003 | Pelrine et al. | |
| 2003/0120353 A1 | 6/2003 | Christensen | |
| 2003/0163206 A1 | 8/2003 | Yasui et al. | |
| 2004/0049290 A1 | 3/2004 | Bedard | |
| 2004/0054423 A1 | 3/2004 | Martin | |
| 2004/0064195 A1 | 4/2004 | Herr | |
| 2004/0064286 A1 | 4/2004 | Levi et al. | |
| 2004/0088057 A1 | 5/2004 | Bedard | |
| 2004/0111163 A1 | 6/2004 | Bedard et al. | |
| 2004/0181289 A1 | 9/2004 | Bedard et al. | |
| 2004/0193286 A1 | 9/2004 | Grundei | |
| 2004/0263127 A1 | 12/2004 | Turner et al. | |
| 2004/0267379 A1 | 12/2004 | Pasolini | |
| 2005/0004495 A1 | 1/2005 | Goswami | |
| 2005/0010139 A1 | 1/2005 | Aminian et al. | |
| 2005/0107889 A1 | 5/2005 | Bedard et al. | |
| 2005/0119763 A1 | 6/2005 | Christensen | |
| 2005/0143838 A1 | 6/2005 | Collier | |
| 2005/0197717 A1 | 9/2005 | Ragnarsdottir et al. | |
| 2005/0283257 A1 | 12/2005 | Bisbee et al. | |
| 2006/0041321 A1 | 2/2006 | Christensen | |
| 2006/0064195 A1 | 3/2006 | Kern et al. | |
| 2006/0069448 A1 | 3/2006 | Yasui | |
| 2006/0136072 A1 | 6/2006 | Bisbee et al. | |
| 2006/0155385 A1 | 7/2006 | Martin | |
| 2006/0173552 A1 | 8/2006 | Roy | |
| 2006/0235544 A1 | 10/2006 | Iversen et al. | |
| 2006/0249315 A1 | 11/2006 | Herr et al. | |
| 2007/0016329 A1 | 1/2007 | Herr et al. | |
| 2007/0027555 A1 | 2/2007 | Palmer et al. | |
| 2007/0043449 A1 | 2/2007 | Herr et al. | |
| 2007/0123997 A1 | 5/2007 | Herr et al. | |
| 2007/0162152 A1 | 7/2007 | Herr et al. | |

FOREIGN PATENT DOCUMENTS

| | | |
|---|---|---|
| DE | 195 21 464 A1 | 6/1995 |
| DE | 197 54 690 A | 7/1999 |
| EP | 0 549 855 A2 | 7/1993 |
| EP | 0 628 296 A2 | 12/1994 |
| EP | 0718951 A | 6/1996 |
| EP | 0902547 A | 3/1999 |
| EP | 1066 793 | 1/2001 |
| EP | 1107420 A | 6/2001 |
| EP | 1 166 726 A1 | 1/2002 |
| EP | 1 169 982 A1 | 1/2002 |
| EP | 1340478 | 9/2003 |
| FR | 2 623 086 A1 | 5/1989 |
| GB | 2 201 260 A | 8/1988 |
| GB | 2 244 006 A | 11/1991 |
| GB | 2 260 495 A | 4/1993 |
| GB | 2 268 070 A | 1/1994 |
| GB | 2 301 776 | 12/1996 |
| GB | 2 302 949 A | 2/1997 |
| GB | 2 367 753 | 8/1998 |
| GB | 2 328 160 A | 2/1999 |
| GB | 2 334 891 A | 9/1999 |
| GB | 2 338 653 A | 12/1999 |
| JP | 11056885 | 3/1999 |
| JP | 11000345 A2 | 6/1999 |
| JP | 20011277175 | 10/2001 |
| JP | 2002-191654 A | 7/2002 |
| WO | WO 93/24080 A1 | 12/1993 |
| WO | WO 94/06374 | 3/1994 |
| WO | WO 95/26171 A1 | 10/1995 |
| WO | WO 96/41598 | 12/1996 |
| WO | WO 96/41599 A | 12/1996 |
| WO | WO 97/00661 A1 | 1/1997 |
| WO | WO 98/25552 | 6/1998 |
| WO | WO 98/38951 A1 | 9/1998 |
| WO | WO 99/05991 A2 | 2/1999 |
| WO | WO 99/08621 A2 | 2/1999 |
| WO | WO 99/29272 | 6/1999 |
| WO | WO 00/27318 A | 5/2000 |
| WO | WO 00/30572 A1 | 6/2000 |
| WO | WO 00/38599 | 7/2000 |
| WO | WO 00/71061 | 11/2000 |
| WO | WO 01/17466 A2 | 3/2001 |
| WO | WO 01/50986 A1 | 7/2001 |
| WO | WO 01/72245 | 10/2001 |
| WO | WO 03/003953 | 1/2003 |
| WO | WO 03/086245 A | 10/2003 |
| WO | WO 03/086245 A2 | 10/2003 |
| WO | WO 03/088373 A | 10/2003 |
| WO | WO 2004/017873 A1 | 3/2004 |
| WO | WO 2005/041819 A2 | 5/2005 |

OTHER PUBLICATIONS

Blaya, J. A., et al., "Adaptive Control of a Variable-Impedance Ankle-Foot Orthosis to Assist Drop-Foot Gait" IEEE Transactions on Neural Systems and Rehabilitation Engineering, vol. 12, No. 1, Mar. 2004, pp. 24-31.

Copes/Bionic Ankle, The Most Significant Development in Ankle Prosthetics in Over a Half Century, 1985.

Dietl, H. Bargehr, Der Einsatz von Elektronik bei Prothesen zur Versorgung der unteren Extremitat, Med. Orth. Tech. 117 1997, pp. 31-35.

Flowers, et al., Journal of Biomechanical Engineering: Transactions of the ASME; Feb. 1977, pp. 3-8.

Proteor, Assembly and Adjustment Instructions for 1P5O-R, pp. 1-21, Sep. 2004.

Suga, T., et al., "Newly designed computer controlled knee-ankle-foot orthosis (Intelligent Orthosis)", Prosthetics and Orthotics International, 1998, 22, 230-239.

Townsend M A et al., "Biomechanics and modeling of bipedal climbing and descending." Journal of Biomechanics 1976, vol. 9, No. 4, pp. 227-239, XP008078405.

"The Electronic C-Leg® Knee Joint System: Instructions for Use," Otto Bock, available at http://www.ottobockus.com/products/lower_limb_prosthetics/c-leg_instructions.pdf, 32 pages (printed Jul. 20, 2006).

"MT9 Inertial 3D Motion Tracker," Xsens Technologies B.V., available at http://www.xsens.com/download/MT9_brochure.pdf (at least as early as Oct. 2004), printed Jul. 20, 2006.

PCT International Search Report and Written Opinion, mailed Apr. 27, 2006, Appl. No. PCT/US2005/046664, 8 pages.

Townsend, M.A. and Tsai T.C., "Biometrics and Modeling of Bipedal Climbing and Descending," *J. Biometrics*, 1976, vol. 9, pp. 227-239.

Samuel K. Au et al., "An EMG-position Controlled System for an Active Ankle-Foot Prosthesis: An Initial Experimental Study," Proceedings of the 2005 IEEE 9th Int'l Conference on Rehabilitation Robotics, Jun. 28-Jul. 1, 2005.

SYSTEMS AND METHODS FOR PROCESSING LIMB MOTION

RELATED APPLICATION

This application claims the benefit of priority under 35 U.S.C. §119(e) of U.S. Provisional Application Ser. No. 60/638,802, filed on Dec. 22, 2004, and entitled "SYSTEMS AND METHODS FOR GAIT DETECTION," the entirety of which is hereby incorporated herein by reference to be considered a part of this specification.

BACKGROUND OF THE INVENTION

1. Field of the Invention

Embodiments of the invention described herein relate generally to limb-motion detection and, in particular, limb-motion detection using a plurality of sensor signals.

2. Description of the Related Art

Millions of individuals worldwide rely on prosthetic and/or orthotic devices to compensate for disabilities, such as amputation or debilitation, and to assist in the rehabilitation of injured limbs. Orthotic devices include external apparatuses used to support, align, prevent, protect, correct deformities of, or improve the function of movable parts of the body. Prosthetic devices include apparatuses used as artificial substitutes for a missing body part, such as an arm or leg.

Conventional orthoses are often used to support a joint, such as an ankle or a knee, of an individual, and movement of the orthosis is generally based solely on the energy expenditure of the user. Some conventional prostheses are equipped with basic controllers that artificially mobilize the joints without any interaction from the amputee and are capable of generating only basic motions. Such basic controllers do not take into consideration the dynamic conditions of the working environment. The passive nature of these conventional prosthetic and orthotic devices typically leads to movement instability, high energy expenditure on the part of the disabled person or amputee, gait deviations and other short- and long-term negative effects. This is especially true for leg orthoses and prostheses.

To address these drawbacks, some prosthetic devices include one or more systems for monitoring the movement of a user. For instance, certain prosthetic knee devices include one or more pressure sensors implanted in an insole for detecting changes in force during user movement. In response to these detected changes in force, a control unit mechanically adjusts the prosthetic knee. Such measurements, however, are generally usable only for analysis of the past gait of the user. Furthermore, because the pressure sensors are generally used to detect contact between the foot and the ground, the pressure sensors are not able to produce usable signals during a swing stage of the foot. In addition, the insole containing the pressure sensors often requires precise placement and alignment in relation to the limb being monitored.

SUMMARY OF THE INVENTION

Accordingly, a need exists for improved systems and methods for detecting and analyzing movement of a device associated with a limb. In particular, a need exists for systems and methods for accurately detecting and/or predicting motion-related events and phases, such as by processing a discrete and/or continuous signal representing a stride of a user during a stance stage and a swing stage. What are also needed are systems for controlling the movement of a device associated with a limb based on the monitored motion of the device.

In certain embodiments, a system is disclosed for analyzing the movement of a device associated with a limb. The system comprises at least one accelerometer configured to generate a time series of motion signals indicative of a movement of a device associated with a limb. The system further comprises a process module in communication with the at least one accelerometer, the process module comprising a filter and a comparison module. The filter is configured to process the time series of motion signals received from the at least one accelerometer and configured to generate a plurality of filtered signals. The comparison module is configured to compare the plurality of filtered signals with a plurality of sample signals, wherein the comparison module is further configured to identify limb-motion events associated with the movement of the device associated with the limb. In certain further embodiments, the system is incorporated into an actuatable prosthetic or orthotic device being movable about a joint, such as, for example, an ankle joint.

In certain embodiments, a method is disclosed for processing signals associated with the movement of a device associated with a limb. The method comprises receiving a time series of motion signals indicative of movement of a device associated with a limb and filtering selected ones of the time series of motion signals. The method further includes processing the filtered signals to identify at least one limb-motion category.

In certain embodiments, a method is disclosed for processing signals associated with the movement of a device associated with a limb. The method includes receiving a plurality of sensor signals indicative of a motion of a device associated with a limb. The method further includes processing the plurality of sensor signals with a time series analysis and comparing the processed sensor signals to a plurality of motion patterns so as to associate the processed sensor signals with a particular motion pattern.

In certain embodiments, a system is disclosed for processing signals associated with the movement of a device associated with a limb. The system includes means for receiving a time series of motion signals indicative of movement of a device associated with a limb. The system further includes means for filtering selected ones of the time series of motion signals and means for processing the filtered signals to identify at least one limb-motion category.

In certain embodiments of the invention, a system is disclosed for processing signals associated with the movement of a prosthetic ankle device. The system includes means for receiving a plurality of sensor signals indicative of a motion of a device associated with a limb. The system further includes means for processing the plurality of sensor signals with a time series analysis and means for comparing the processed sensor signals to a plurality of motion patterns so as to associate the processed sensor signals with a particular motion pattern.

Another embodiment of the invention includes a machine loadable software program for a processor for controlling the movement of a device associated with a limb. The software program includes an input module, a filter module, a comparison module, and a control module. The input module is configured to receive a time series of motion signals. The filter module is configured to process the time series of motion signals and is configured to generate a plurality of filtered signals. The comparison module is configured to compare the plurality of filtered signals with a plurality of sample signals and configured to generate a gait event selection signal indicative of the movement of a device associated with a limb. The control module is configured to generate a control signal based at least in part on the gait event selection signal, wherein the control signal is capable of causing the movement of the device associated with the limb. The software module may include, for example, an autoregressive (AR) filter and/or a Kalman filter. The time series of motion signals may be indicative of acceleration in at least one direction of the device associated with the limb.

For purposes of summarizing the invention, certain aspects, advantages and novel features of the invention have been described herein. It is to be understood that not necessarily all such advantages may be achieved in accordance with any particular embodiment of the invention. Thus, the invention may be embodied or carried out in a manner that achieves or optimizes one advantage or group of advantages as taught herein without necessarily achieving other advantages as may be taught or suggested herein.

DETAILED DESCRIPTION OF PREFERRED EMBODIMENTS

Figure 1:
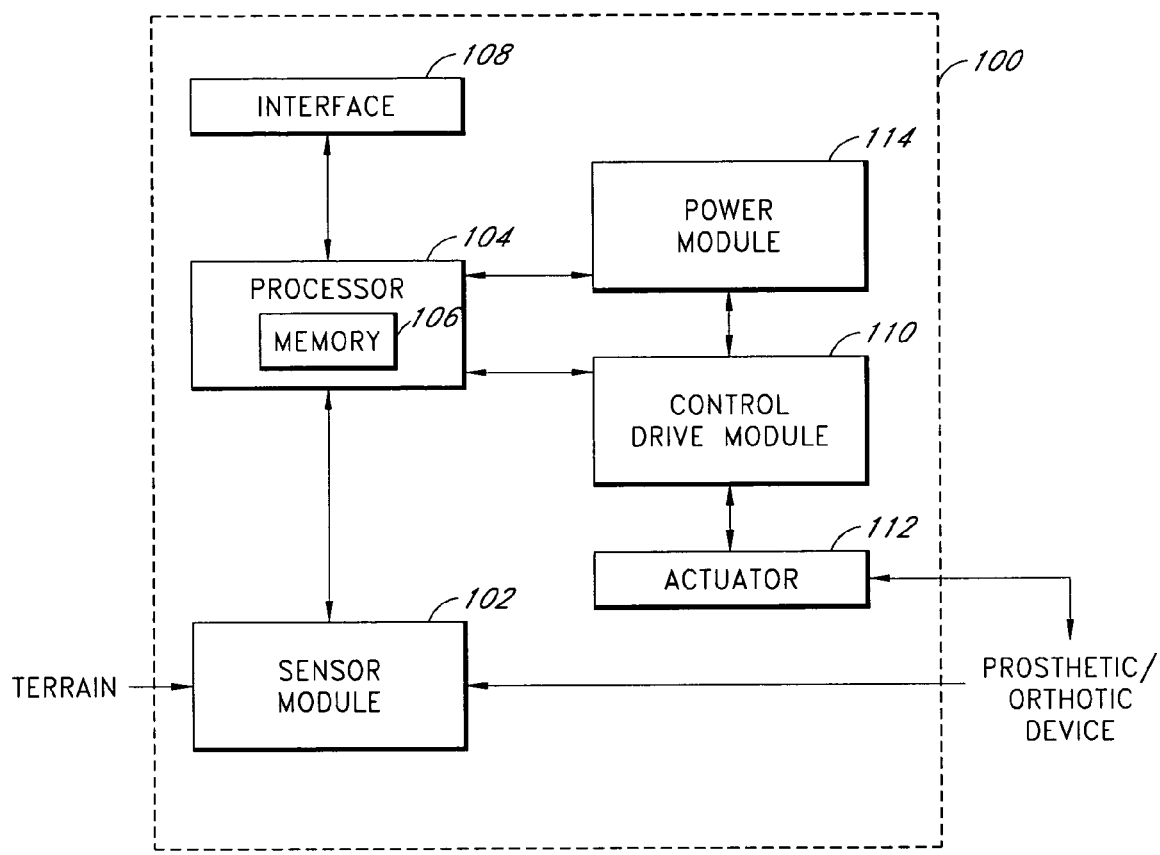
FIG. 1 illustrates a block diagram of a system architecture of a control system for a prosthetic/orthotic device according to certain embodiments of the invention.

Embodiments of the invention disclosed herein relate generally to limb-motion detection, and in particular, to determining the gait of a user to control, such as in real time, an actuatable prosthetic or orthotic device. In certain embodiments, the invention is used to identify a gait pattern of a user, a gait state and/or a terrain on which the user is traveling. While the description sets forth various embodiment-specific details, it will be appreciated that the description is illustrative only and should not be construed in any way as limiting the invention. Furthermore, various applications of the invention, and modifications thereto, which may occur to those who are skilled in the art, are also encompassed by the general concepts described herein.

The features of the system and method will now be described with reference to the drawings summarized above. Throughout the drawings, reference numbers are reused to indicate correspondence between referenced elements. The drawings, associated descriptions, and specific implementation are provided to illustrate embodiments of the invention and not to limit the scope of the disclosure.

Moreover, methods and functions described herein are not limited to any particular sequence, and the acts or blocks relating thereto can be performed in other sequences that are appropriate. For example, described acts or blocks may be performed in an order other than that specifically disclosed, or multiple acts or blocks may be combined in a single act or block.

The terms "prosthetic" and "prosthesis" as used herein are broad terms and are used in their ordinary sense and refer to, without limitation, any system, device or apparatus usable as an artificial substitute or support for a body part.

The term "orthotic" and "orthosis" as used herein are broad terms and are used in their ordinary sense and refer to, without limitation, any system, device or apparatus usable to support, align, prevent, protect, correct deformities of, immobilize, or improve the function of parts of the body, such as joints and/or limbs.

The term "coronal" as used herein is a broad term and is used in its ordinary sense and relates to any description, location, or direction relating to, situated in, or being in or near the plane that passes through the long axis of the body. A "coronal plane" may also refer to any plane that passes vertically or approximately vertically through the body and is perpendicular or approximately perpendicular to the median plane and that divides the body into anterior and posterior sections.

The term "sagittal" as used herein is a broad term and is used in its ordinary sense and relates to any description, location, or direction relating to, situated in, or being in or near the median plane (i.e., the plane divides the body lengthwise into right and left halves) or any plane parallel or approximately parallel thereto. A "sagittal plane" may also refer to any vertical anterior to posterior plane that passes through the body parallel or approximately parallel to the median plane and that divides the body into equal or unequal right and left sections.

The term "transverse" as used herein with respect to physiology is a broad term and is used in its ordinary sense and relates to any description, location, or direction relating to, situated in, or being in or near a plane that divides the body into top and bottom portions or any plane parallel or approximately parallel thereto. A "transverse plane" may also refer to any horizontal or substantially horizontal plane that divides the body into equal or unequal top and bottom sections.

The term "time series" as used herein is a broad term and is used in its ordinary sense and includes, without limitation, a plurality of data points spaced apart at uniform or substantially uniform time intervals. Such data points may be in a continuous (with either a uniform or a non-uniform sampling rate) and/or a sequential (discrete) form. A "time series analysis" comprises a method for processing a time series of signals to determine patterns of trend and/or forecast (predict) one or more values.

The terms "limb-motion event" and "gait event" as used herein are broad terms and are used in their ordinary sense and relate to, without limitation, distinct positions of a limb during movement, such as during a gait cycle. For example, a gait event for a stride of an individual may include toe off, heel strike, midswing, or the like.

The terms "limb-motion phase," "gait phase," "limb-motion category" and "gait category" as used herein are broad terms and are used in their ordinary sense and relate to, without limitation, forms or categories of limb movement. For example, a gait phase for a stride may include level ground walking, walking up or down stairs, walking up or down ramps, running and the like.

FIG. 1 illustrates a block diagram of one embodiment of a system architecture of a control system 100 for a prosthetic/orthotic device. In certain embodiments, the control system 100 is usable with a lower limb prosthesis, such as, for example, an ankle-motion controlled prosthetic device described in U.S. application Ser. No. 11/056,344, filed Feb. 11, 2005, entitled "SYSTEM AND METHOD FOR MOTION-CONTROLLED FOOT UNIT," and published on Sep. 8, 2005, as U.S. Patent Publication No. 20050197717A1, which is hereby incorporated herein by reference in its entirety to be considered a part of this specification. In other embodiments, the control system 100 is usable by an orthotic system or a rehabilitation system having a motion-controlled foot or other motion-controlled limb.

As depicted in FIG. 1, the control system 100 includes a sensor module 102, a processor 104, a memory 106, an interface 108, a control drive module 110, an actuator 112 and a power module 114. In certain embodiments, the control system 100 processes data received from the sensor module 102 with the processor 104. The processor 104 communicates with the control drive module 110 to control the operation of the actuator 112 to mimic natural joint movement (e.g., by adjusting the prosthetic/orthotic device): Furthermore, the control system 100 may predict how the prosthetic/orthotic device may need to be adjusted in order to accommodate movement by the user. The processor 104 may also receive commands from a user and/or other device through the interface 108. The power module 114 provides power to the other components of the control system 100.

FIG. 1 illustrates the sensor module 102 communicating with the processor 104. In certain embodiments, the sensor module 102 advantageously provides measurement data to the processor 104 and/or to other components of the control system 100. For example, the sensor module 102 may be coupled to a transmitter, such as, for example, a BLUETOOTH® transmitter, that sends the sensed measurements to the processor 104. In other embodiments, other types of transmitters or wireless technology may be used, such as infrared, WIFI®, or radio frequency (RF) technology. In other embodiments, wired technologies may be used to communicate with the processor 104.

In certain embodiments, the sensor module 102 measures variables relating to the prosthetic/orthotic device, such as the position and/or the movement of the prosthetic/orthotic device during one or more portions of a gait cycle. For instance, the sensor module 102 may be advantageously located on the prosthetic/orthotic device, such as near a mechanical ankle center of rotation.

In other embodiments, the sensor module 102 may be located on the user's natural limb that is attached to, or associated with, the prosthetic/orthotic device. In such an embodiment, the sensor module is used to capture information relating to the movement of the user's natural limb to appropriately adjust the prosthetic/orthotic device. For example, the control system 100 may detect the gait of the user and adjust the prosthetic/orthotic device accordingly while the prosthetic/orthotic device is in a swing stage of the first step. In other embodiments of the invention, there may be a latency period in which the control system 100 requires one or two strides before being able to accurately determine the gait of the user and to adjust the prosthetic/orthotic device appropriately.

Furthermore, the sensor module 102 may be used to capture information relating to, for example, one or more of the following: the position of the prosthetic/orthotic device with respect to the ground; the inclination angle of the prosthetic/orthotic device; the direction of gravity with respect to the position of the prosthetic/orthotic device; information that relates to a stride of the user, such as when the prosthetic/orthotic device contacts the ground (e.g., "heel strike" or "toe strike"), is in mid-stride or midswing, or leaves the ground (e.g., "toe off" or "heel off"), the distance between the prosthetic/orthotic device and the ground at the peak of the swing stage (i.e., the maximum height during the swing stage); the timing of the peak of the swing stage; combinations of the same and the like.

In certain preferred embodiments, the sensor module 102 provides a time series of motion signals relating to the real-time movement of the device associated with the limb. For instance, the sensor module 102 may comprise one or more accelerometers that produce a continuous and/or a discrete time series of motions signals to be analyzed by the processor 104, which process is described in more detail below.

As depicted in FIG. 1, in certain embodiments of the invention, the sensor module 102 is further configured to measure environmental or terrain variables including one or more of the following: the characteristics of the ground surface, the angle of the ground surface, the air temperature and wind resistance. In certain embodiments, the measured temperature may also be used to calibrate the gain and/or bias of other sensors.

The output signal(s) of the sensor module 102 may be generated at any predefined rate. For instance, in certain embodiments, the sensor module 102 generates a 100 Hz output signal representing the gait of a user. In other embodiments, the output signal(s) of the sensor module 102 may be greater than, or less than, 100 Hz. In yet other embodiments, the frequency of the sensor output(s) may vary between different portions of a user's movement (e.g., stride). Furthermore, changes in the frequency of the sensor module output signal may be compensated for by modifying normal data stored in the memory and used in comparison(s) with the received sensor module signal.

The processor 104 advantageously processes data received from other components and/or modules of the control system 100. In certain embodiments, the processor 104 receives information from the sensor module 102 relating to movement (e.g., gait) of the user. In turn, the processor 104 may use such movement data to determine one or more characteristics of the limb-motion of the user and/or to send commands to the control drive module 110. For example, the data captured by the sensor module 102 may be used to generate a waveform comprising a time series of data points that portray information relating to the gait or movement of a limb of the user. Subsequent changes to the waveform may be identified by the processor 104 to predict future movement of the user and to adjust the prosthetic/orthotic device accordingly.

In certain embodiments, the processor 104 may perform signal processing to detect one or more motion-related events. For instance, signals relating to the sensing of movement of a prosthetic/orthotic foot may be used to detect one or more gait stride events, which may include, for example, heel strike, toe down, heel off, initial push off, toe off, start of a forward swing, mid forward swing, end of forward swing and/or heel strike preparation.

In certain embodiments, the processor 104 may perform signal processing to detect one or more motion-related phases or categories. For example, detected gait events and/or the received time series of motion signals may be analyzed in real time to determine a motion-related phase or category. In certain embodiments, signals relating to the sensing of movement of a prosthetic/orthotic foot may be used to detect one or more locomotion phases which may include, for example, walking on level ground, walking up stairs and/or down stairs, and/or walking up an incline and/or down a decline. In other embodiments, additional phases or categories may be detected, such as one or more of the following: lying down, cycling, climbing a ladder, running or the like.

In other embodiments, the processor 104 may perform a variety of other processing functions. For example, the processor 104 may use information received from the sensor module 102 to detect stumbling by the user. The processor 104 may function as a manager of communication between the components of the control system 100. For example, the processor 104 may act as the master device for a communication bus between multiple components of the control system 100 and/or provide power distribution and/or conversion to the other components of the control system 100.

In addition, the processor 104 may function so as to temporarily suspend or decrease power to the control system 100 when a user is in a sitting or a standing position. Such control provides for energy conservation during periods of decreased use. The processor 104 may also process error handling, such as when communication fails between components, an unrecognized signal or waveform is received from the sensor module 102, or when feedback from the control drive module 110 or the prosthetic/orthotic device causes an error or appears corrupt.

In certain embodiments, the processor 104 generates a security factor when analyzing information received from the sensor module 102 and/or when sending commands to the control drive module 110. For example, the security factor may include one of a range of values that reflects a degree of certainty of a determination made by the processor 104. For instance, a high security value may indicate a higher degree of certainty associated with a determined motion-related event or phase, and a low security factor may indicate a lower degree of certainty as to the determined event or phase. In certain embodiments, subsequent adjustments of the prosthetic/orthotic device are not made unless the event and/or phase of the user is recognized with a security factor above a predetermined threshold value.

The processor 104 may include modules that comprise logic embodied in hardware or firmware, or that comprise a collection of software instructions written in a programming language, such as, for example C++. A software module may be compiled and linked into an executable program, installed in a dynamic link library, or may be written in an interpretive language such as BASIC. It will be appreciated that software modules may be callable from other modules or from themselves, and/or may be invoked in response to detected events or interrupts. Software instructions may be embedded in firmware, such as an EPROM or EEPROM. It will be further appreciated that hardware modules may be comprised of connected logic units, such as gates and flip-flops, and/or may be comprised of programmable units, such as programmable gate arrays or processors.

With continued reference to FIG. 1, the processor 104 further includes a memory 106 for storing instructions and/or data. In certain embodiments, the memory 106 preferably is configured to store data representing gait patterns or curves. For example, the memory 106 may include experimental data representing gait curves generated from a plurality of data sets relating to a plurality of individuals, which experimental data is stored for comparison in motion-related event and/or phase detection. Experimental data may be gathered in a laboratory setting and/or in association with the particular control system 100. In further embodiments, such data may also be used for initial calibration of the control system 100.

In yet other embodiments, the memory 106 may further store one or more of the following types of data or instructions: an error log for the other components of the control system 100; information regarding past activity of the user (e.g., number of steps); control parameters and set points; information regarding software debugging or upgrading; pre-programmed algorithms for basic movements of the prosthetic or orthotic system; calibration values and parameters relating to the sensor module 102 or other components; instructions downloaded from an external device; combinations of the same or the like.

The memory 106 may comprise any buffer, computing device, or system capable of storing computer instructions and/or data for access by another computing device or a computer processor. In certain embodiment, the memory 106 is a cache memory. In other embodiments of the invention, the memory 106 comprises random access memory (RAM) or may comprise other integrated and accessible memory devices, such as, for example, read-only memory (ROM), programmable ROM (PROM), and electrically erasable programmable ROM (EEPROM). In yet other embodiments, at least a portion of the memory 106 may be separate from the processor 104. For instance, the memory 106 may comprise a removable memory, such as a memory card, a removable drive, or the like.

As illustrated, the processor 104 also communicates with the interface 108, such as, for example, to receive user- or activity-specific instructions from a user or from an external device. For instance, the processor 104 may communicate with a personal computer, a personal digital assistant, a cell phone, a portable computing device, or the like, to download or receive operating instructions. In certain embodiments, the interface 108 may comprise a network interface or a Universal Serial Bus (USB) connector.

The control drive module 110 translates high-level plans or instructions received from the processor 104 into low-level control signals to be sent to the actuator 112. In certain embodiments, the control drive module 110 comprises a printed circuit board that implements control algorithms and tasks related to the management of the actuator 112. The control drive module 110 may also be used to provide feedback to the processor 104 regarding the position or movement of the actuator 112 or prosthetic/orthotic device.

The actuator 112 provides for the controlled movement of the prosthetic/orthotic device. For instance, the actuator 112 may advantageously control movement of the prosthetic/orthotic device to execute angular and/or rotational displacements synchronized with the user's movement or locomotion. For example, the actuator 112 may be similar to one of the actuators described in copending U.S. application Ser. No. 11/056,344, filed Feb. 11, 2005.

The power module 114 includes one or more sources and/or connectors usable to power the control system 100. In one embodiment, the power module 114 is advantageously portable, and may include, for example, a rechargeable battery. As illustrated, the power module 114 communicates with the control drive module 110 and the processor 104. In other embodiments, the power module 114 communicates with other control system 100 components instead of, or in combination with, the control drive module 110 and the processor 104. For example, in one embodiment, the power module 114 communicates directly with the sensor module 102. Furthermore, the power module 114 may communicate with the interface 108 such that a user is capable of directly controlling the power supplied to one or more components of the control system 100.

While the control system 100 has been described with reference to certain embodiments, other variations of the control system 100 may be used. For example, the control system 100 may operate without the interface 108. Furthermore, in certain embodiments, the control system 100 is based on a distributed processing system wherein the different functions performed by the prosthetic/orthotic system, such as sensing, data processing, and actuation, are performed or controlled by multiple processors that communicate with each other. In yet other embodiments, the processed data may be used to trigger an action other than movement, such as, for example, the illumination of a diode or the emitting of an alarm or an audible alert.

It is also contemplated that the components of the control system 100 may be integrated in different forms. For example, the components can be separated into several sub-components or can be separated into more devices that reside at different locations and that communicate with each other, such as through a wired or wireless network. For example, in one embodiment, the modules may communicate through RS232 or serial peripheral interface (SPI) channels. Multiple components may also be combined into a single component.

With continued reference to the control system 100 of FIG. 1, in certain embodiments of the invention, the sensor module 102 provides data relating to the linear acceleration and/or angular acceleration of a prosthetic/orthotic device, and such data is used to determine one or more motion-related events and phases and/or to appropriately adjust the prosthetic/orthotic device. For instance, one or more sensors of the sensor module 102 may measure acceleration of the prosthetic/orthotic device in three substantially, mutually perpendicular axes. For example, three accelerometers may be used to measure acceleration in the three orthogonal axes to sense motion of the prosthetic/orthotic device and to generate an associated time series of motion signals.

Various aspects of the received time series signal(s) may be used by the processor 104. For example, in certain embodiments, the processor uses the signal itself, a first derivative (e.g., slope) and/or a second derivative (e.g., slope rate) thereof to determine a motion-related event and/or phase.

With reference to a prosthetic/orthotic foot device, linear acceleration detection may include sensing downward acceleration (e.g., along an x-axis), forward acceleration (e.g., along a y-axis) and inward acceleration (e.g., along a z-axis) from the perspective of the left foot of the user. For instance, detection of linear acceleration may be performed according to the following three equations:

$\frac{\partial^2 x}{\partial t}$ : downward acceleration $\frac{\partial^2 y}{\partial t}$ : forward acceleration $\frac{\partial^2 z}{\partial t}$ : inward acceleration In certain embodiments, both the downward acceleration and the forward acceleration measurements are used by the processor 104 to estimate a motion-related event and/or phase of a user. In certain embodiments, the inward acceleration measurement is used by the processor 104 for quality control to determine if the sensing module 102 is properly calibrated and/or positioned or is working correctly.

Furthermore, the sensing module 102 may also detect angular acceleration, such as angular acceleration in three substantially orthogonal planes. For instance, with reference to a prosthetic/orthotic foot device, angular acceleration may include sensing, with one or more accelerometers (e.g., one or more gyroscopes), in a transverse (x-y) plane, in a coronal plane (y-z) and in a sagittal plane (e-x) of a user. In certain embodiments, detection of angular acceleration is performed according to the following three equations:

$\frac{\partial^2 \theta_x}{\partial t}$ : angular acceleration in transverse plane $\frac{\partial^2 \theta_y}{\partial t}$ : angular acceleration in coronal plane $\frac{\partial^2 z}{\partial t}$ : angular acceleration in sagittal plane In certain embodiments, either or both of the angular accelerations in the transverse and coronal planes are used to estimate a quality of detection by the sensing module 102. The angular acceleration in the sagittal plane may be used to estimate motion-related events and/or phases of the user.

In certain embodiments, one or more acceleration sensors may include an XSENS acceleration sensor, such as the MT9 Inertial 3D motion tracker commercially available from XSENS Motion technologies (Netherlands). In yet other embodiments, other suitable types of acceleration or movement reading sensors may also be used. For example, the sensor module 102 may include a gyroscope configured to measure angular speed. In other embodiments, the sensor module 102 includes a plantar pressure sensor configured to measure, for example, the vertical plantar pressure of a specific underfoot area. Other movement signal(s) in a given reference plane can also be utilized, such as, for example, measurements of centrifugal force, magnetic field and/or electromagnetic field.

In yet other embodiments, the sensor module 102 may include one or more of the following in place of, or in combination with, at least one accelerometer: kinematic sensors, multi- and/or single-axis gyroscopes, multi-axis accelerometers, load sensors, flex sensors or myoelectric sensors that may be configured to capture data from the user's natural limb. U.S. Pat. No. 5,955,667, U.S. Pat. No. 6,301,964, and U.S. Pat. No. 6,513,381, also illustrate examples of sensors that may be used with embodiments of the invention, which patents are herein incorporated by reference in their entireties.

Furthermore, in certain embodiments of the invention, the sensor module 102 may be configured to monitor motion of a limb (or a device associated with a limb) with respect to a global reference instead of, or in combination with, the local tracking of movement. For example, the sensor module 102 may include a sensor that detects movement with respect to another reference plane or object, such as the earth, as is done in global positioning systems (GPS).

Figure 2A:
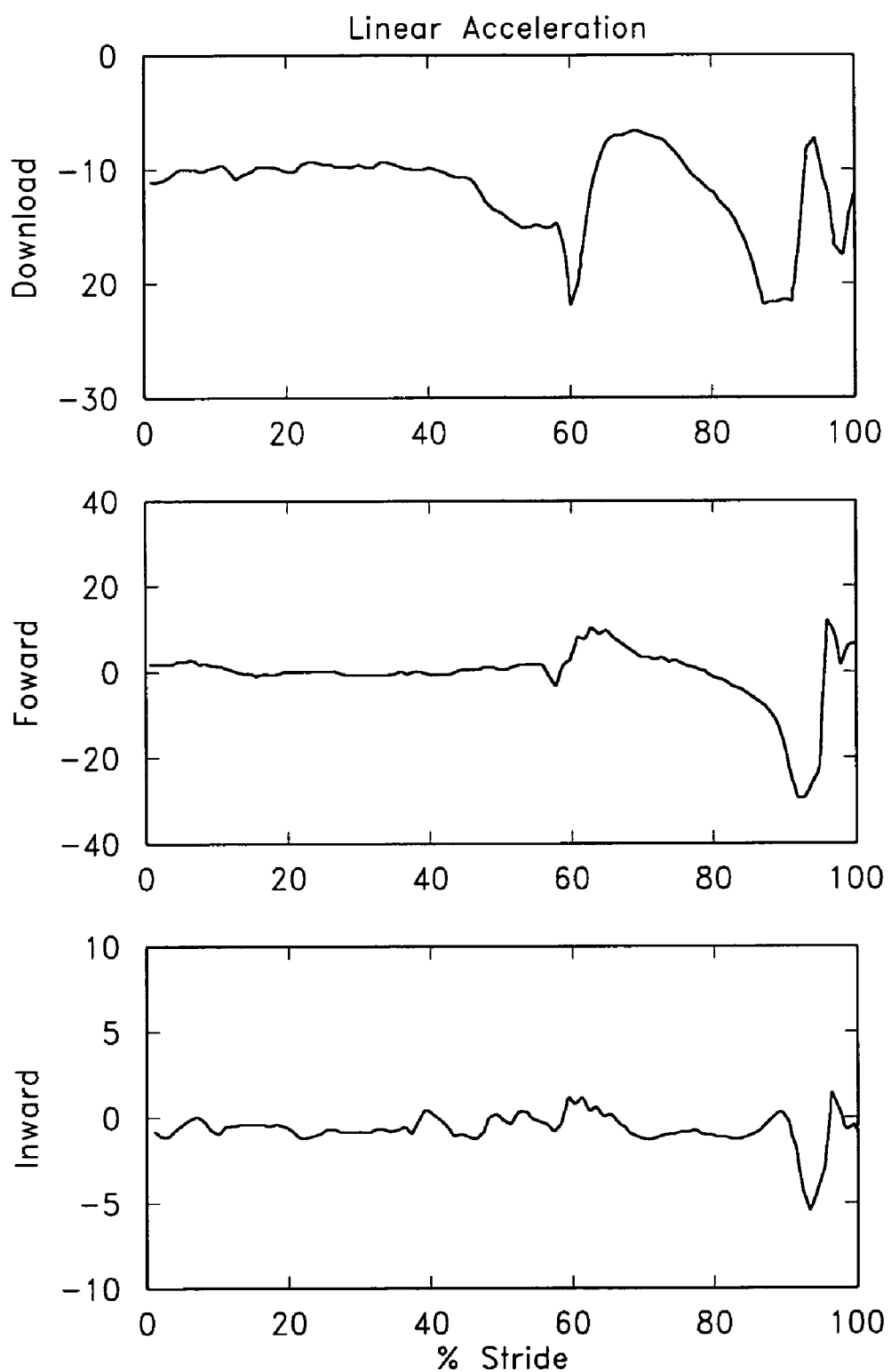
FIGS. 2A and 2B illustrate exemplary data detection sets relating to level ground walking by a user.
Figure 2B:
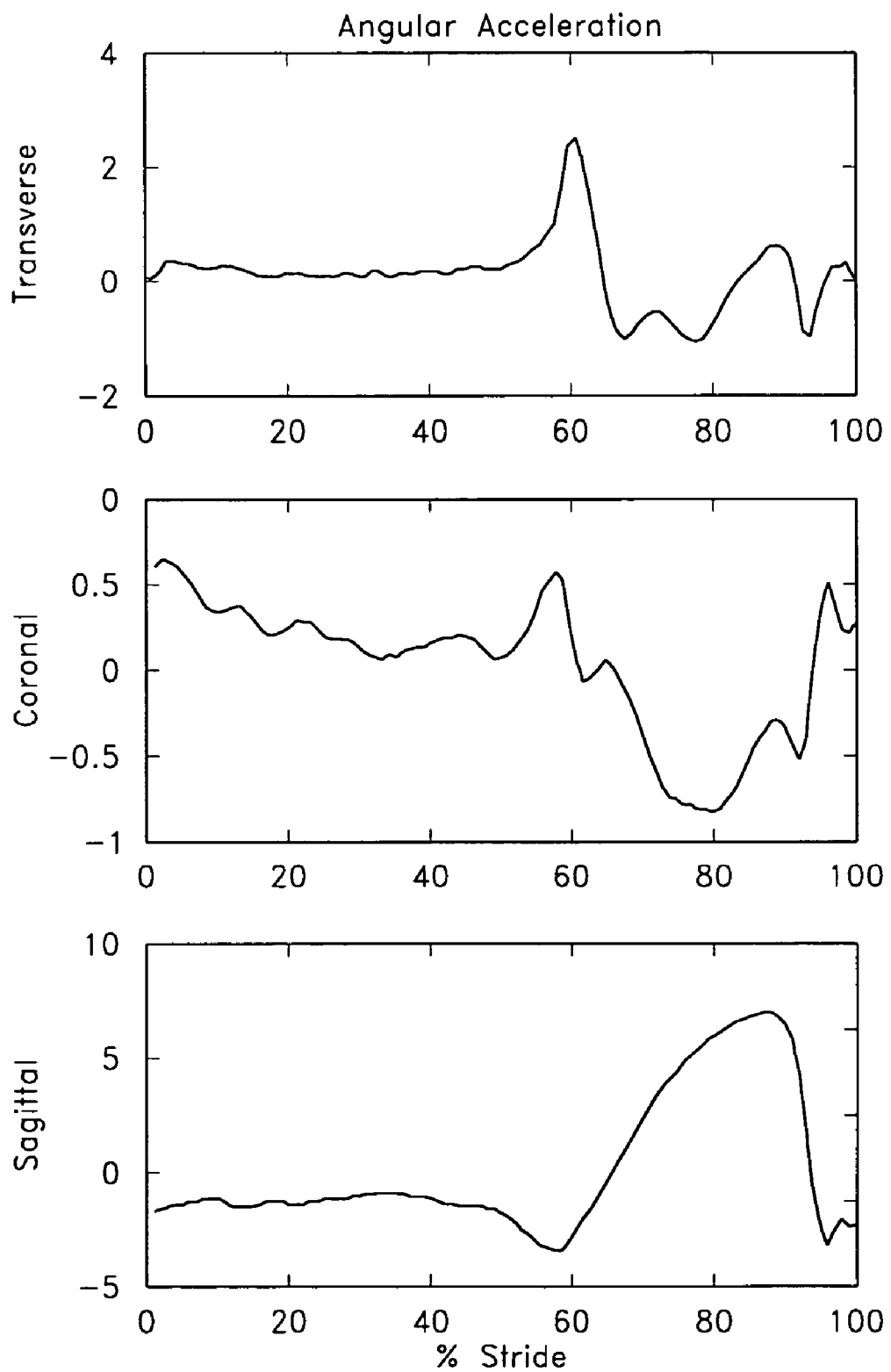

FIGS. 2A and 2B illustrate exemplary data detection sets relating to level ground walking by a user and include, for example, signals indicative of the motion of a prosthetic foot. As shown, the six graphs illustrate relative measurements of linear acceleration (i.e., downward, forward and inward directions) and angular acceleration (i.e., transverse, coronal and sagittal planes). In certain embodiments of the invention, such data sets are generated by the sensor module 102 and are further analyzed by the processor 104 to determine characteristics of the gait of the user. In other embodiments of the invention, other received signals may relate to motion of another type of prosthetic limb (e.g., an arm) or relate to the motion of orthotic devices.

In certain embodiments of the invention, the processor 104 advantageously performs a time series analysis on the sensed motion signals, or data points relating thereto, to determine characteristics of a gait of a user. Such a time series analysis includes processing the sequence(s) of received measurements (e.g., acceleration measurements) with the general assumptions that the measurements follow non-random orders and that successive values in the received sensor data represent consecutive measurements taken at equally spaced time intervals.

For example, in certain preferred embodiments, one or more data points of the received time series of motion signals is associated with one or more timestamps that identify portions of the signal for normalization and/or for comparison with stored data signals. The timestamps allow for different signals having similar timestamps to be compared and processed by the processor 104. For instance, the one or more timestamps associated with the received sensor signal may be based on a detected or determined limb-motion event (e.g., a heel strike or a toe-off event). That is, the timestamp correlates the associated data point with a particular point in time after the determined event has occurred.

The timestamps also preferably allow data sets having a different number of values (e.g., a different rate) to be compared by the processor 104. For example, a received time series of motion signals may have a data set of eighty points for a particular duration of time, while a stored data set may include one hundred points for the same duration. By correlating the timestamps between the two data sets, the processor 104 is able to appropriately expand and/or shift the received data set, such as by interpolation, to have the same number of data points as, and to line up in time with, the stored data set.

Figure 3:
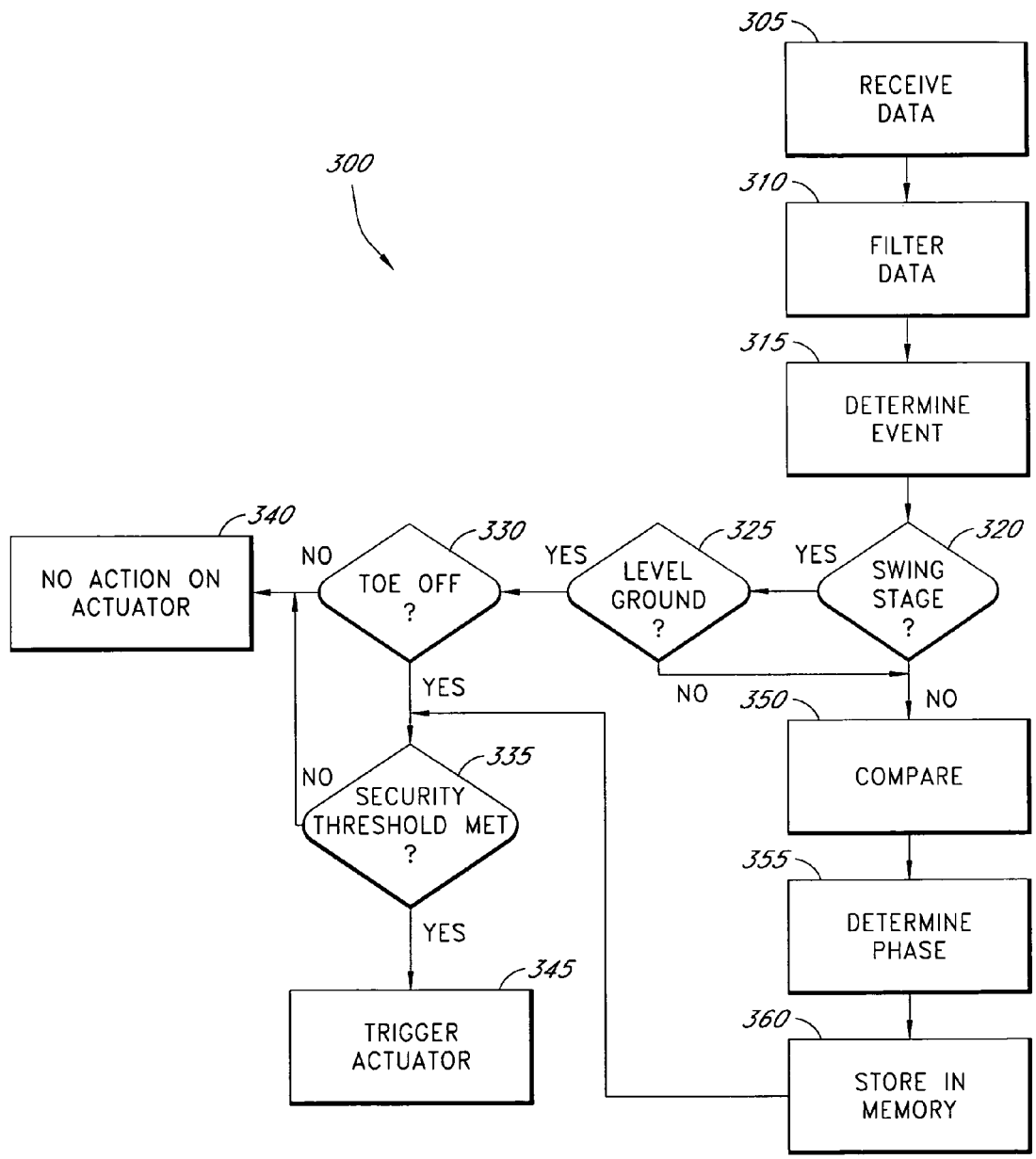
FIG. 3 illustrates a flowchart of an exemplary embodiment of a gait stride detection process executable by the control system of FIG. 1.

FIG. 3 illustrates an exemplary flowchart of a gait stride detection process 300. In certain embodiments, the gait detection process 300 is performed at least in part by the control system 100 of FIG. 1 to determine a motion-related event and/or phase of a user and to appropriately adjust an actuating mechanism of a corresponding prosthetic/orthotic device. For exemplary purposes, the gait detection process 300 will be described with reference to the components of the control system 100 in the context of a motion-controlled prosthetic foot. A skilled artisan, however, will recognize from the disclosure herein a wide variety of other hardware and/or software systems or devices capable of performing at least a portion of the gait detection process 300.

The gait detection process 300 begins with block 305, wherein the processor 104 receives measurement data from the sensor module 102. In certain embodiments, the measurement data comprises linear acceleration data and/or angular acceleration data sensed with respect to the movement of the prosthetic ankle device. For instance, measurement data may include at least the following six subsets of data received from at least one accelerometer positioned on the prosthetic ankle device: linear acceleration data in the downward, forward and inward directions; and angular acceleration data in the transverse, coronal and sagittal planes. In other embodiments, the measurement data may relate to the movement of a healthy limb and be used to control the movement of a corresponding artificial limb.

In certain embodiments, the measurement data is preferably received as a time series of data points, wherein the measurement data includes a sequence of data points ordered in the time in which they were observed. In certain embodiments, the time series of data points is a discrete time series set wherein acceleration measurements of the prosthetic device are taken every 10 milliseconds. In yet other embodiments, other frequencies of measurements may be used and/or the frequency of measurements may be variable over a particular period of time and/or during particular portions of the user's gait. In yet other embodiments, the received data may be in the form of a continuous time series with either a uniform or non-uniform sampling rate.

After receiving the measurement data, the processor 104 preferably filters the data (block 310) in order to predict future data points and/or to provide a smoother signal for the subsequent detection routines. In certain embodiments, such filtering may include predictive, static and/or adaptive filtering. For instance, an autoregressive (AR) filter, such as for example, a Kalman filter, may process the last "n" data points in the received motion signal to remove random error. In such embodiments, the filter may determine how much weight is to be given to each of a number of past data points in performing the current data analysis. This advantageously provides for a smoother signal by filtering out fluctuation in the signal (e.g., noise) and signal abnormalities. For instance, the filter may determine that, during the processing of a current data input, forty percent of the value associated with the previous (last) data point is to be used, thirty percent of the value associated with the second-to-last data point is to be used, fifteen percent of the value associated with the third-to-last data point is to be used, and so forth.

In other embodiments, the received measurement data may be processed by other regressive techniques (e.g., linear, k'th order polynomial, quadratic, exponential, harmonic) and/or other filters (e.g., moving average (MA), autoregressive moving average (ARMA), autoregressive integrated moving average (ARIMA), low pass, high pass, fuzzy, combinations of the same and the like) for producing a smoother signal.

For example, in certain embodiments, an autoregressive filter is used to calculate the slope of a received time series of motion signals related to linear acceleration and/or a rate of turn (slope rate) of a received time series of motion signals related to angular acceleration. This calculated data may then be used to determine a current motion-related event. For instance, in certain embodiments, the processor 104 uses the following equations to calculate the slope and slope rate for at least one time series of motion signals:

$$AR := [\, ar_0 \ \ ar_1 \ \ \ldots \ \ ar_i \ \ \ldots \ \ ar_n \,] \qquad \sum_{i=0}^{n} ar_i = 1$$

$$\frac{\partial}{\partial t}\left(\frac{\partial^2 X_{l,j}}{\partial t^2}\right) = \sum_{k=j-n}^{j} \frac{1}{\Delta t}\left(\frac{\partial^2 X_{l,k}}{\partial t^2} - \frac{\partial^2 X_{l,k-1}}{\partial t^2}\right) AR_{j-k} \qquad j \geq n+1$$

$$\frac{\partial^2}{\partial t^2}\left(\frac{\partial^2 X_{l,j}}{\partial t^2}\right) = \sum_{k=j-n}^{n} \frac{1}{\Delta t^2} \frac{\left(\frac{\partial^2 X_{l,k}}{\partial t^2} - 2\frac{\partial^2 X_{l,k-1}}{\partial t^2} + \frac{\partial^2 X_{l,k-2}}{\partial t^2}\right)}{\Delta t^2} AR_{j-k} \qquad j \geq n+2$$

-continued $$\frac{\partial^2 X_{i,j}}{\partial t^2} := \begin{bmatrix} \frac{\partial x_1^2}{\partial t^2} & \frac{\partial y_1^2}{\partial t^2} & \frac{\partial z_1^2}{\partial t^2} & \frac{\partial \theta_{x,1}^2}{\partial t^2} & \frac{\partial \theta_{y,1}^2}{\partial t^2} & \frac{\partial \theta_{z,1}^2}{\partial t^2} \\ \frac{\partial x_2^2}{\partial t^2} & \frac{\partial y_2^2}{\partial t^2} & \frac{\partial z_2^2}{\partial t^2} & \frac{\partial \theta_{x,2}^2}{\partial t^2} & \frac{\partial \theta_{y,2}^2}{\partial t^2} & \frac{\partial \theta_{z,2}^2}{\partial t^2} \\ \frac{\partial x_3^2}{\partial t^2} & \frac{\partial y_3^2}{\partial t^2} & \frac{\partial z_3^2}{\partial t^2} & \frac{\partial \theta_{x,3}^2}{\partial t^2} & \frac{\partial \theta_{y,3}^2}{\partial t^2} & \frac{\partial \theta_{z,3}^2}{\partial t^2} \\ \vdots & \vdots & \vdots & \vdots & \vdots & \vdots \\ \frac{\partial x_m^2}{\partial t^2} & \frac{\partial y_m^2}{\partial t^2} & \frac{\partial z_m^2}{\partial t^2} & \frac{\partial \theta_{x,m}^2}{\partial t^2} & \frac{\partial \theta_{y,m}^2}{\partial t^2} & \frac{\partial \theta_{z,m}^2}{\partial t^2} \end{bmatrix} \quad j = 1 \ldots N$$

wherein n is a number of data points; AR is a vector holding n data point values that determine how much weight is given to past data values so as to filter the signal prior to further processing; X is a position matrix of the monitored object; j is a relative position in time of a particular data point; t is time; and Δt is a time between data points (e.g., ten milliseconds). The bottom equation shown above comprises a signal matrix that may be used to process a variety of forms of data (e.g., acceleration and/or gyroscope data) representing an activity measurement signal.

In yet other embodiments, different filtering techniques may be used with different data sets and/or during different detected motion-related events. For example, linear acceleration signals may undergo a different filter process than angular acceleration signals received during the same time period.

In yet other embodiments, each motion-related event is associated with its own stored data set. Each data set may, in turn, include a plurality of parameters for comparison with the received time series of motion signals. For instance, each data set relating to event recognition may include between three or more parameters, such as, for example, between three and twelve parameters. Generally, the more parameters that are used in the data comparison, the more accurate is the event and/or phase detection.

For instance, the parameters may include values and their first and second derivatives received from between two and six motion sensors. For example, in an embodiment, one of the parameters may include a slope of the downward acceleration when threshold values of a gyroscope signal have been met in the sagittal plane. Such may further trigger the processing of forward acceleration data and the rate of turn of the forward acceleration.

Such parameters may also be used in determining a security value for the event and/or phase determination. If several or all of the parameters are met in a comparison between a stored data set and a received time series of motion signals, the processor 104 may generate a high security value indicating a high likelihood that an accurate determination of the event and/or phase has been made. Likewise, if two parameters are used and/or set in such a comparison, the processor 104 may generate a low security value.

After the data has been received and/or filtered, the processor 104 determines a motion-related event based on the received data (block 315). For instance, processor 104 may detect an ankle-motion related event of the corresponding prosthetic ankle device, such as, for example, heel strike, toe down, heel off, toe off, mid-swing or end of swing.

If the event detected by the processor 104 is related to a swing stage (block 320), the gait detection process moves to block 325. The processor 104 then determines if the user is walking on level ground. If the processor 104 determines that the user in walking on level ground, the gait detection process 300 proceeds with block 330. At block 330, the processor 104 determines if there has been a toe-off event (e.g., the "toe" of the prosthetic foot leaving the ground during a stride). If there has been a toe-off event detected, the processor 104 determines if a security threshold has been met (block 335). For example, in determining the toe-off event, the processor 104 may also generate a security value, as discussed previously, that represents the probability or percent certainty that the toe-off event has been correctly detected.

If the security value is not above a particular threshold (e.g., low likelihood of correctness of determination), or if the processor 104 does not detect a toe-off event at block 330, the gait detection process 300 moves to block 340, and no action is taken on the actuator 112. For instance, an actuator of the prosthetic ankle device may be kept in its current state or position, or the actuator may automatically return to a default state or position.

If the security value does meet the predetermined threshold in block 335, the gait detection process 300 moves to block 345. At block 345, the processor 104 outputs commands for appropriately adjusting the actuator 112. For example, the processor 104 may output a signal to the control drive module 110 to cause the prosthetic ankle device to dorsiflex such that the toe of the device is raised after toe-off.

With reference to block 325, if the user is not walking on level ground, or if the event detected by the processor 104 at block 320 is not related to a swing stage, the gait detection process 300 proceeds with block 350. At block 350, the processor 104 compares the received time series data with stored measurement data. For instance, the memory 106 may store normal data for a plurality of different motion-related phases, which normal data is then compared with a normalized version of the received data in order to determine the current phase. In certain embodiments, the memory 106 includes normal data relating to level ground walking, incline and decline walking, and walking up and down stairs. Furthermore, the normal data may be based on information that is general to all users, or the normal data may be determined from previous strides of the particular user.

In certain embodiments, the received time series of motion signals is normalized by the processor 104 according to the following equations:

$$DataNorm = \begin{bmatrix} \frac{\partial^2 x_1'}{\partial t^2} & \frac{\partial^2 y_1'}{\partial t^2} & \frac{\partial^2 z_1'}{\partial t^2} & \frac{\partial^2 \theta_{x,1}'}{\partial t^2} & \frac{\partial^2 \theta_{y,1}'}{\partial t^2} & \frac{\partial^2 \theta_{z,1}'}{\partial t^2} & S_1' \\ \vdots & \vdots & \vdots & \vdots & \vdots & \vdots & \vdots \\ \frac{\partial^2 x_N'}{\partial t^2} & \frac{\partial^2 y_N'}{\partial t^2} & \frac{\partial^2 z_N'}{\partial t^2} & \frac{\partial^2 \theta_{x,N}'}{\partial t^2} & \frac{\partial^2 \theta_{y,N}'}{\partial t^2} & \frac{\partial^2 \theta_{z,N}'}{\partial t^2} & S_N' \end{bmatrix}$$

-continued $$dt = \frac{L-k}{n-1}, t'_i = t'_{i-1} + dt, t = \lfloor t'_i \rfloor, \xi = t - t'_i$$

$$\frac{\partial^2 x'_i}{\partial t^2} = \frac{\partial^2 x_{tw-1}}{\partial t^2}\xi + \frac{\partial^2 x_{tw}}{\partial t^2}(1-\xi), \frac{\partial^2 \theta'_{x,i}}{\partial t^2} = \frac{\partial^2 \theta_{x,tw-1}}{\partial t^2}\xi + \frac{\partial^2 \theta_{x,tw}}{\partial t^2}(1-\xi),$$

$$\frac{\partial^2 y'_i}{\partial t^2} = \frac{\partial^2 y_{tw-1}}{\partial t^2}\xi + \frac{\partial^2 y_{tw}}{\partial t^2}(1-\xi), \frac{\partial^2 \theta'_{y,i}}{\partial t^2} = \frac{\partial^2 \theta_{y,tw-1}}{\partial t^2}\xi + \frac{\partial^2 \theta_{y,tw}}{\partial t^2}(1-\xi),$$

$$\frac{\partial^2 z'_i}{\partial t^2} = \frac{\partial^2 z_{tw-1}}{\partial t^2}\xi + \frac{\partial^2 z_{tw}}{\partial t^2}(1-\xi), \frac{\partial^2 \theta'_{y,i}}{\partial t^2} = \frac{\partial^2 \theta_{y,tw-1}}{\partial t^2}\xi + \frac{\partial^2 \theta_{y,tw}}{\partial t^2}(1-\xi),$$

$$S'_i = S_{tw}, \quad i = 0 \ldots N$$

wherein ∂t is a difference in time between data points; L is an end stream point identifier (e.g., end of stride); k is a start stream point identifier (e.g., beginning of stride); n is a number of points in a corresponding comparison data matrix; t'_i is a new timestamp in a normalized data matrix; and ξ is a distance from the new timestamp to time points of the normalized dataset. Moreover, the top equation illustrated above represents an information matrix for raw data received from sensors, such as from the sensor module 102.

Once the received data has been normalized, the processor 104 is able to compare the normalized data with the stored normal data (e.g., in the comparison matrix) for different phases in order to determine the current motion-related phase of the user (block 355). For instance, the processor 104 may determine from the comparison the type of surface on which the user is walking (e.g., ramp, stairs; level ground) and/or the slope of the surface.

After the current phase is determined, the gait detection process 300 proceeds with block 360, wherein the processor 104 stores in the memory 106 the received data, the determined event, the determined phase, a security value and/or timestamps associated with the received time series signal. For example, in certain embodiments, the processor 104 may store data from multiple strides, such as the previous three strides of the user. This information stored in the memory 106 may then be preferably used in future data processing, such as during the comparison routine at block 350.

The gait detection process 300 then moves to block 335 to determine if a security threshold has been met for the determined phase. If the generated security value is not above the predetermined threshold, the gait detection process 300 moves to block 340, and no action is taken on the actuator 112. If the security value does meet the predetermined threshold in block 335, the gait detection process 300 moves to block 345. At block 345, the processor 104 outputs commands for appropriately adjusting the actuator 112 based on the determined phase.

Figure 4:
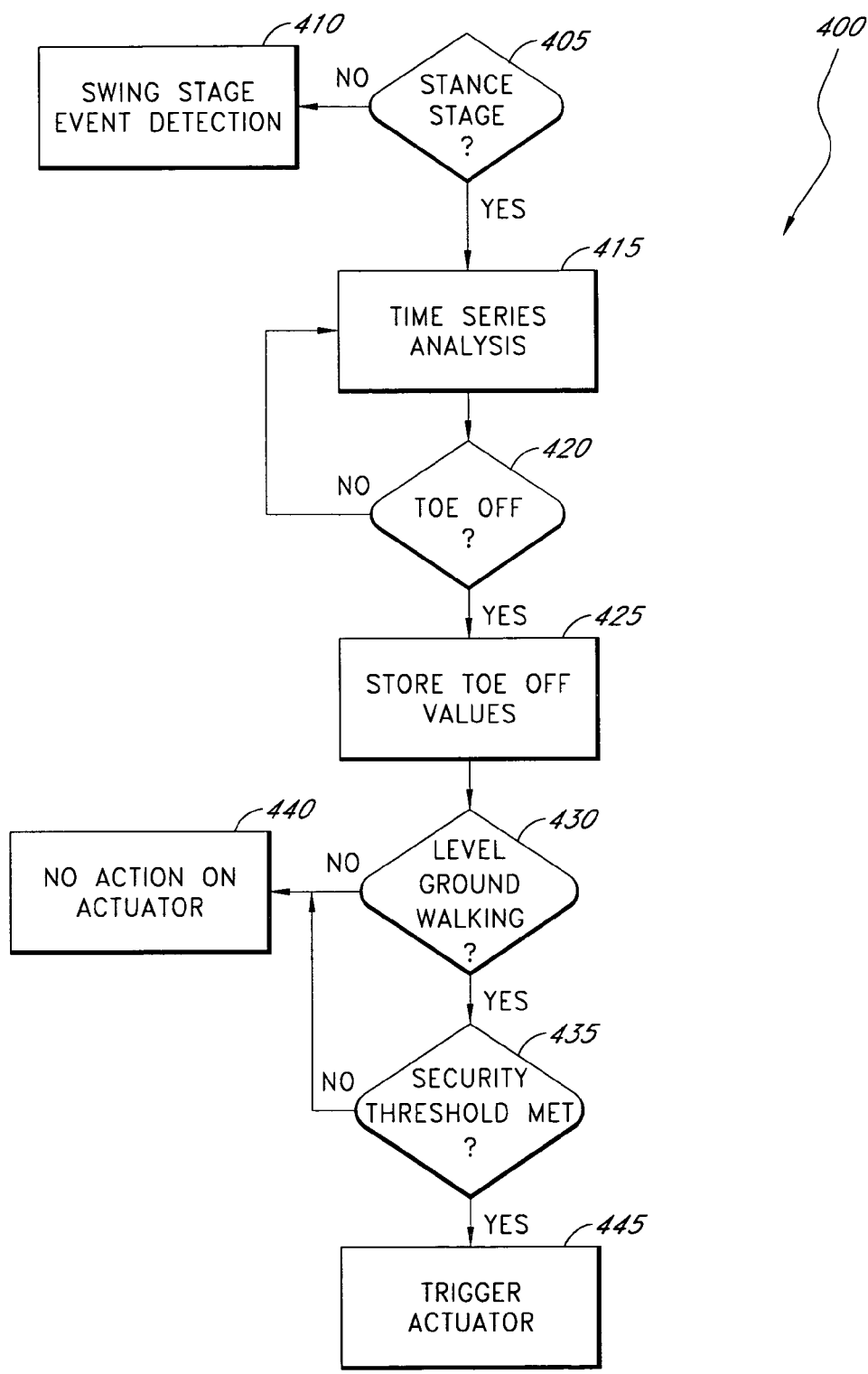
FIG. 4 illustrates a flowchart of an exemplary embodiment of an event detection process executable by the control system of FIG. 1.

FIG. 4 illustrates a flowchart of an exemplary event detection process 400 according to certain embodiments of the invention. For instance, the event detection process 400 may be at least partially performed during blocks 315-345 of the gait stride detection process 300 of FIG. 3. For exemplary purposes, the event detection process 400 will be described with reference to the components of the control system 100 in the context of a motion-controlled prosthetic foot. In particular, the event detection process 400 will be described with reference to detecting a toe-off event of the motion-controlled prosthetic foot. A skilled artisan, however, will recognize from the disclosure herein a wide variety of other hardware and/or software systems or devices capable of performing at least a portion of the event detection process 400.

The event detection process 400 begins at block 405 by determining if the prosthetic foot device is in a stance stage. That is, the processor 104 determines from received measurement data if at least a portion of the prosthetic foot device is in contact with the ground. If the prosthetic foot device is not in a stance stage, the event detection process 400 moves to block 410 to perform swing stage event detection. If the prosthetic foot device is in a stance stage, the event detection process 400 proceeds with block 415. At block 415, the processor 415 performs a time series analysis on the received measurement data, such as is discussed above. For instance, the processor 104 may use a Kalman filter to process the received time series of motion signals.

At block 420, the processor 104 determines if a toe-off event has taken place. If a toe-off event has not occurred, the event detection process 400 returns to block 415 wherein the processor 104 continues to analyze received data. If a toe-off event has occurred, the processor 104 stores the toe-off values in the memory 106 (block 425).

At block 430, the processor 104 then determines if the user is walking on level ground, such as by, for example, analyzing the received measurement data. If the user is walking on level ground, the processor 104 then determines if the security threshold has been met (block 435). For instance, in certain embodiments, the processor 104 produces at least one security value when determining a motion-related event and/or phase. Such a security value may represent the probability or percent certainty that the particular event or phase has been correctly detected.

If the generated security value does not meet or exceed the predetermined threshold, or if at block 430 the processor 104 does not determine that the user is walking on level ground, the event detection process 400 moves to block 440, and no action is taken on the actuator 112. If, however, the security threshold is met, the processor 104 outputs commands for appropriately adjusting the actuator 112 (block 445). For example, the processor 104 may output a signal to the control drive module 110 to cause the prosthetic ankle device to dorsiflex such that the toe of the device is raised after toe off.

Figure 5A:
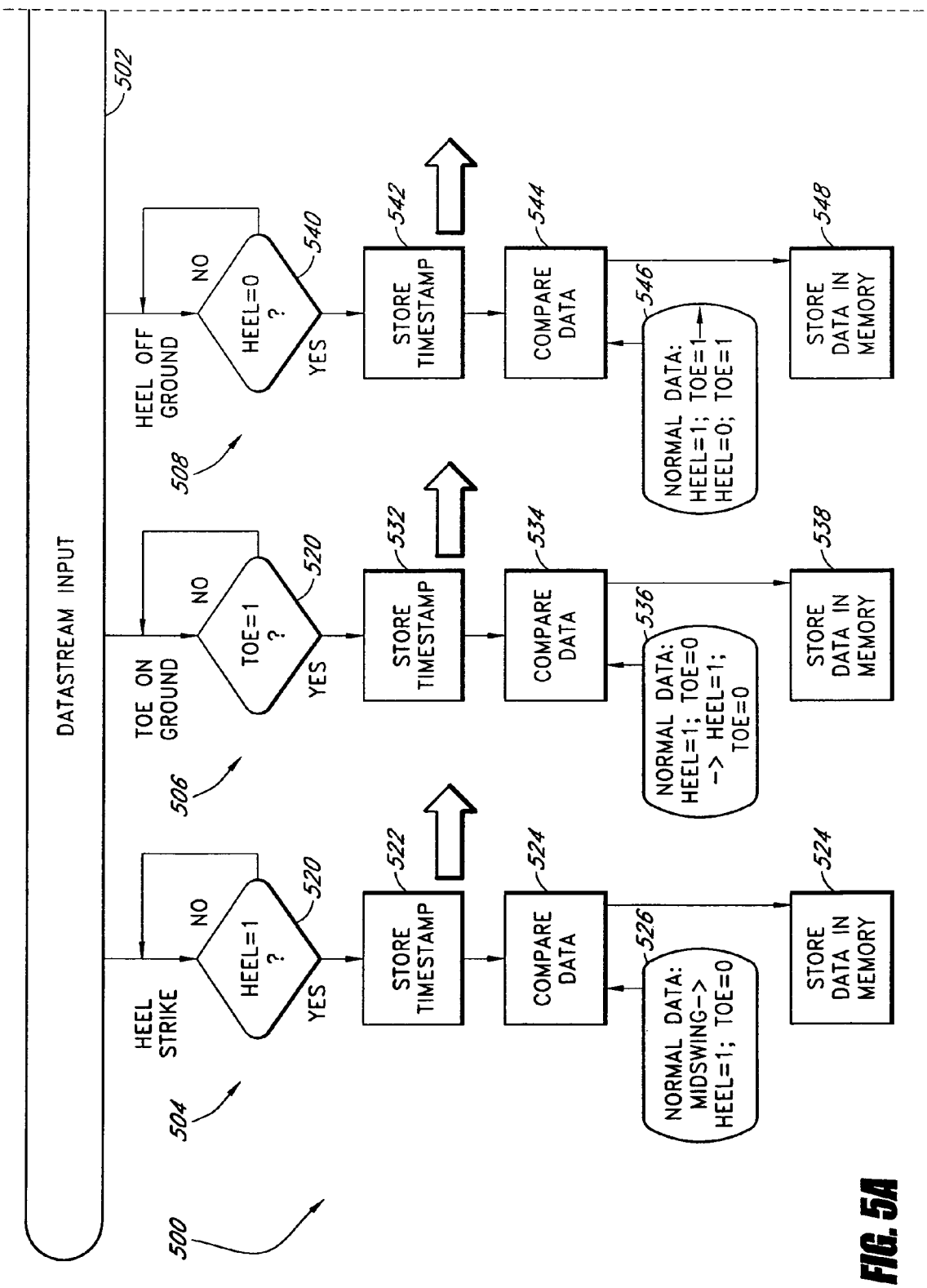
FIGS. 5A and 5B illustrate a dataflow diagram of an exemplary embodiment of a data comparison process executable by the control system of FIG. 1.
Figure 5B:
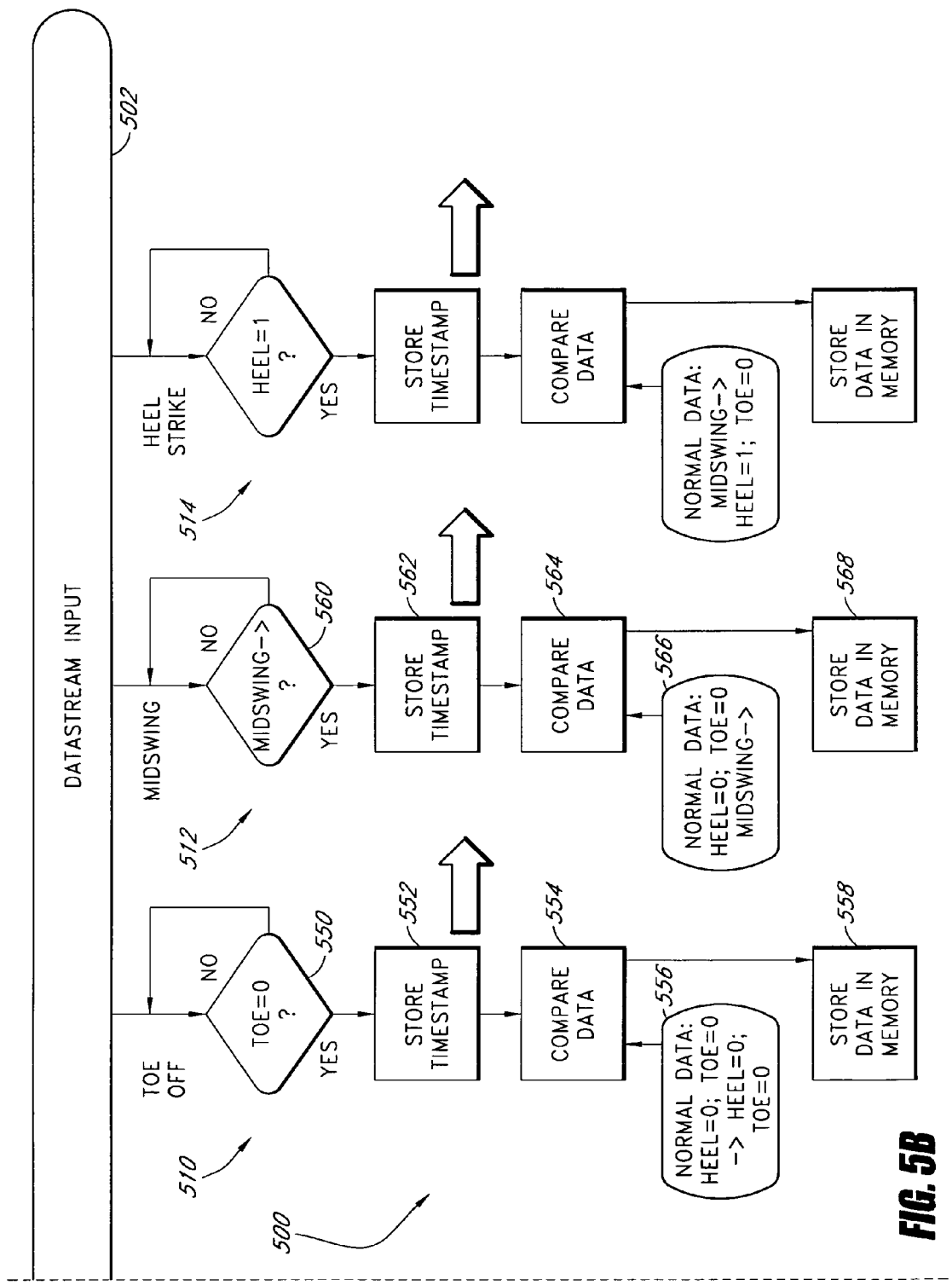

FIGS. 5A and 5B illustrate a dataflow diagram of data comparison process 500 according to certain embodiments of the invention. For example, the comparison process 500 may be performed at least in part during several of the blocks (e.g., blocks 315, 320, 330 and 350) of the gait stride detection process 300 of FIG. 3. For exemplary purposes, the data comparison process 500 will be discussed with reference to detecting and processing gait events relating to a motion-controlled prosthetic foot. A skilled artisan, however, will recognize from the disclosure herein a wide variety of other hardware and/or software systems or devices capable of performing at least a portion of the comparison process 500.

The illustrated comparison process 500 includes a data stream input 502 that includes information relating to movement of the motion-controlled prosthetic foot. In certain embodiments, the data stream input comprises at least one time series of data signals indicative of acceleration (e.g., linear acceleration and/or angular acceleration) of the prosthetic foot.

As shown, the comparison process 500 includes several different routines, each of which relates to a motion-related event of the prosthetic foot. In particular, the comparison process 500 includes a heel-strike routine 504, a toe-on-ground routine 506, a heel-off-ground routine 508, a toe off routine 510, a midswing routine 512 and a second heel-strike routine 514. As is also illustrated, the time from the heel-strike event to the toe-off event is labeled as a stance stage, and the time from the toe-off event to the heel-strike event is labeled as a swing stage.

In certain embodiments, the data stream input 502 is received by all the routines at substantially the same time for further processing and event detection. In general, the data flow of the comparison process 500 occurs from left to right, as illustrated by the block arrows in FIGS. 5A and 5B. For example, during normal level ground walking, the processing and detection of a heel-strike event will occur prior to the processing and detection of a toe-on-ground event. In certain embodiments, the detection routine of one particular event is not triggered or initiated unless the previous gait event has been detected.

As shown in FIGS. 5A and 5B, the comparison process 500 utilizes a "HEEL" variable and a "TOE" variable to process the data stream input information 502. In particular, the HEEL variable is assigned a value of "1" when the processor 104 determines that the heel portion of the prosthetic foot device is in contact with the ground. The HEEL variable is assigned a value of "0" when the processor 104 determines that the heel of the prosthetic foot device is not in contact with the ground (e.g., is in a swing stage). Likewise, the TOE variable is assigned a value of "1" when the processor 104 determines that the toe portion of the prosthetic foot device is in contact with the ground. The TOE variable is assigned a value of "0" when the processor 104 determines that the toe of the prosthetic foot device is not in contact with the ground (e.g., is in a swing stage).

In certain embodiments, the values of the HEEL and/or TOE variables are derived from acceleration measurements received by the processor. In yet other embodiments, pressure sensors placed near the toe and the heel portions of the prosthetic foot device are used to set the values for the TOE and HEEL variables.

As illustrated, the heel-strike routine 504 begins at block 520 by determining if the HEEL variable has changed from a "0" value to a "1" value, indicating contact of the heel with a ground surface. If the HEEL variable remains a "0" value, the heel-strike routine 504 continues with block 520.

If the heel-strike routine 504 does detect a transition in the value of the HEEL variable from "0" to "1," the processor 104 then stores a timestamp of this change in the memory 106 (block 522). Furthermore, the processor 104 compares (at block 524) the received data stream input data with stored normal data (block 526). As shown, the normal data comprises data that relates to a heel-strike event, wherein there is a transition from a midswing stage (e.g., both HEEL and TOE are equal to "0") to a stage wherein HEEL equals "1" and TOE equals "0." For instance, the normal data may comprise previously recorded and processed data for the particular prosthetic foot. In other embodiments, the normal data may be generalized data applicable to a wide variety of users.

In certain embodiments, each of the distinct gait events is advantageously associated with its own normal data. This is especially useful in situations wherein the quality of data differs between the gait events. For example, it may be easier to accurately determine when a heel-strike event occurs than when a midswing event occurs, and the quality of data may be different for each event.

Once the received data has been compared with the stored data, the processor 104 determines if a true heel-strike event has occurred, and the processor 104 stores the new generated data, such as in the memory 106 (block 528). This stored data can then be used in later comparisons of the heel-strike routine 504.

Once a heel-strike event has been detected, the comparison process 500 proceeds with the toe-on-ground routine 506. The toe-on-ground routine 506 begins at block 530 by determining if the TOE variable has changed from a "0" value to a "1" value, indicating contact of the toe portion with a ground surface. If the TOE variable remains a "0" value, the toe-on-ground routine 506 continues with block 530.

If the toe-on-ground routine 506 does detect a transition in the value of the TOE variable from "0" to "1," the processor 104 then stores a timestamp of this change in the memory 106 (block 532). Furthermore, the processor 104 compares (at block 534) the received data stream input data with stored normal data (block 536). As shown, the normal data comprises data that relates to a toe-on-ground event, wherein there is a transition in the value of the TOE variable from "0" to "1" and wherein the HEEL variable remains equal to Once the received data has been compared with the stored data, the processor 104 determines if a true toe-on-ground event has occurred, and the processor 104 stores the new generated data, such as in the memory 106 (block 538). This stored data can then be used in later comparisons of the toe-on-ground routine 506.

Once a toe-on-ground event has been detected, the comparison process 500 proceeds with the heel-off-ground routine 508. The heel-off-ground routine 508 begins at block 540 by determining if the HEEL variable has changed from a "1" value to a "0" value, indicating a separation between the heel portion of the prosthetic device and a ground surface. If the HEEL variable remains a "1" value, the heel-off-ground routine 508 continues with block 540.

If the heel-off-ground routine 508 does detect a transition in the value of the HEEL variable from "1" to "0," the processor 104 then stores a timestamp of this change in the memory 106 (block 542). Furthermore, the processor 104 compares (at block 544) the received data stream input data with stored normal data (block 546). As shown, the normal data comprises data that relates to a heel-off-ground event, wherein there is a transition in the value of the HEEL variable from "1" to "0" and wherein the TOE variable remains equal to Once the received data has been compared with the stored data, the processor 104 determines if a true heel-off-ground event has occurred, and the processor 104 stores the new generated data, such as in the memory 106 (block 548). This stored data can then be used in later comparisons of the heel-off-ground routine 508.

Once a heel-off-ground event has been detected, the comparison process 500 proceeds with the toe-off-ground routine 510. The toe-off-ground routine 510 begins at block 550 by determining if the TOE variable has changed from a "1" value to a "0" value, indicating a separation between the toe portion of the prosthetic device and a ground surface. If the TOE variable remains a "1" value, the toe-off-ground routine 510 continues with block 550.

If the toe-off-ground routine 510 does detect a transition in the value of the TOE variable from "1" to "0," the processor 104 then stores a timestamp of this change in the memory 106 (block 552). Furthermore, the processor 104 compares (at block 554) the received data stream input data with stored normal data (block 556). As shown, the normal data comprises data that relates to a toe-off-ground event wherein there is a transition in the value of the TOE variable from "1" to "0" and wherein the HEEL variable remains equal to Once the received data has been compared with the stored data, the processor 104 determines if a true toe-off-ground event has occurred, and the processor 104 stores the new generated data, such as in the memory 106 (block 558). This stored data can then be used in later comparisons of the toe-off-ground routine 510.

Once a toe-off-ground event has been detected, the comparison process 500 proceeds with the midswing routine 512. The midswing routine 510 begins at block 550 by determining if a midswing state has been attained. For example, in certain embodiments, the processor 104 may analyze how much time has passed since the detection of the toe-off-ground event (e.g., how long the prosthetic foot has not been contacting the ground) to determine what point the user reach in his or her swing. For instance, if the swing stage of a user's stride has averaged approximately one second, the processor may determine the midswing state to be approximately 0.5 second after the detection of the toe-off-ground event.

In other embodiments, the processor 104 may analyze acceleration measurements to detect a midswing state. For instance, the processor 104 may process linear acceleration measurements in the downward and/or forward directions to determine when the prosthetic foot has reached the peak position of the swing and has begun to move toward the ground surface. If the midswing state has still not been reached, the midswing routine 512 continues with block 560.

If the midswing state has been reached, the processor 104 then stores a timestamp of this point in the memory 106 (block 562). Furthermore, the processor 104 compares (at block 564) the received data stream input data with stored normal data (block 566). As shown, the normal data comprises data that relates to a detected midswing event, wherein TOE variable and the HEEL variable are both equal to "0."

Once the received data has been compared with the stored data, the processor 104 determines if a true midswing event has occurred, and the processor 104 stores the new generated data, such as in the memory 106 (block 568). This stored data can then be used in later comparisons of the midswing routine 512.

Once a midswing event has been detected, the comparison process 500 returns to a heel-strike routine, which is illustrated in FIGS. 5A and 5B as the second heel-strike routine 514. The second heel-strike routine 514 is generally the same as the heel-strike routine 504. That is, the second heel-strike routine 514 begins by determining if the HEEL variable has changed from a "0" value to a "1" value, indicating contact between the heel portion of the prosthetic device and the ground surface. As can be seen, the routines of the comparison process 500 may be repeated, as appropriate, throughout the gait of the user.

Figure 6:
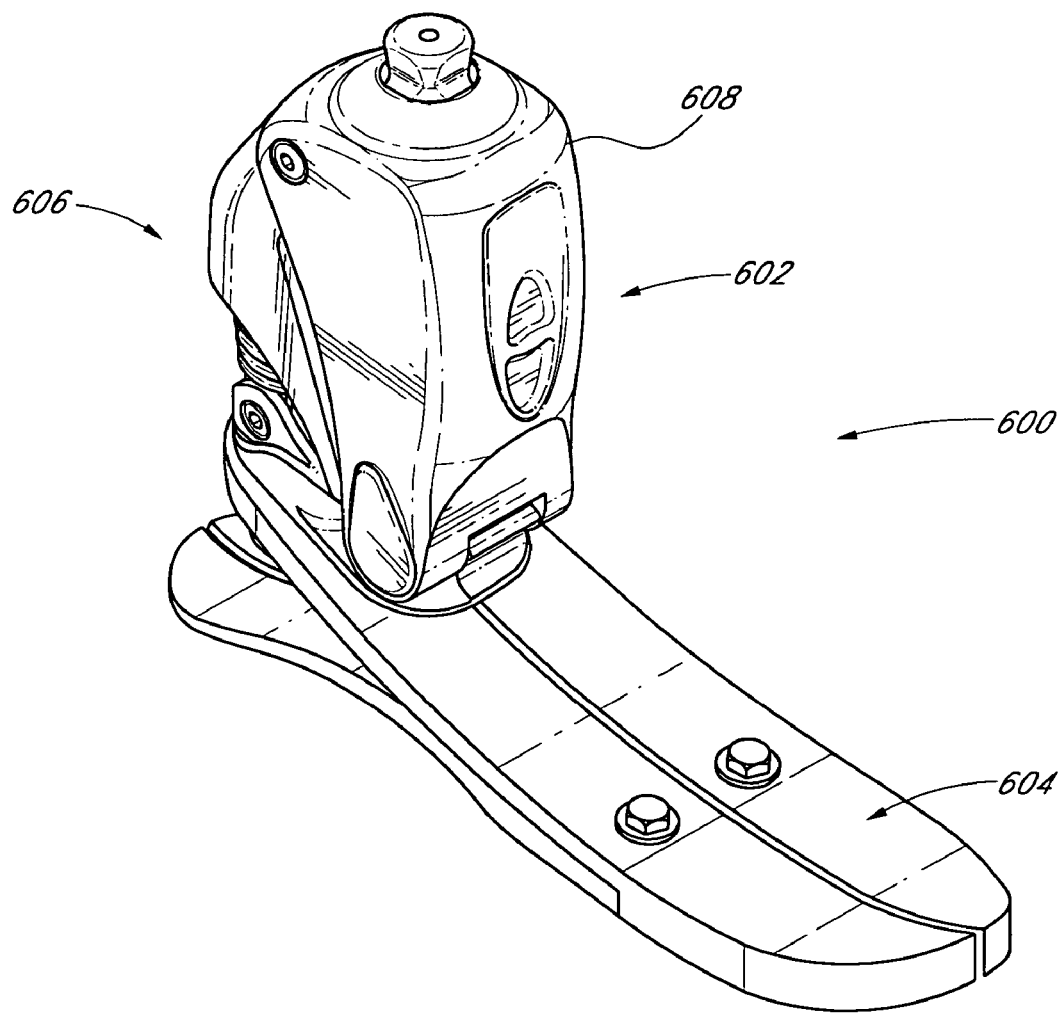
FIG. 6 illustrates a perspective view of an exemplary embodiment of a lower-limb prosthesis usable with the control system of FIG. 1.

FIG. 6 illustrates an exemplary embodiment of a lower-limb prosthesis usable with embodiments of the present invention. In particular, FIG. 6 illustrates a prosthetic ankle device 600 having a lower limb member 602 coupled to a foot unit 604. In certain embodiments, an actuator 606 actively controls an angle between the lower limb member 602 and the foot unit 604 based on control signals received from a processor, as described in more detail previously. In certain embodiments, a frame 608 houses a sensor module, such as the sensor module 102 of FIG. 1, which may include one or more sensors usable to monitor motion of the prosthetic ankle device 600. Further details of motion-controlled foot units usable with embodiments of the invention are disclosed in U.S. patent application Ser. No. 11/219,317, filed Sep. 1, 2005, and entitled "ACTUATOR ASSEMBLY FOR PROSTHETIC OR ORTHOTIC JOINT," and U.S. patent application Ser. No. 11/218,923, filed Sep. 1, 2005, and entitled "SENSING SYSTEM AND METHOD FOR MOTION-CONTROLLED FOOT UNIT," each of which is hereby incorporated herein by reference in its entirety to be considered a part of this specification.

It is contemplated that the above-described systems may be implemented in prosthetic or orthotic systems other than transtibial, or below-the-knee, systems. For example, in one embodiment of the invention, the prosthetic or orthotic system may be used in a transfemoral, or above-the-knee, system, such as is disclosed in U.S. patent application Ser. No. 11/123,870, filed May 6, 2005, and entitled "MAGNETORHEOLOGICALLY ACTUATED PROSTHETIC KNEE;" U.S. patent application Ser. No. 11/077,177, filed Mar. 9, 2005, and entitled "CONTROL SYSTEM AND METHOD FOR A PROSTHETIC KNEE;" U.S. Pat. No. 6,764,520, issued on Jul. 20, 2004, and entitled "ELECTRONICALLY CONTROLLED PROSTHETIC KNEE;" and U.S. Pat. No. 6,610,101, issued Aug. 26, 2003, and entitled "SPEED-ADAPTIVE AND PATIENT-ADAPTIVE PROSTHETIC KNEE," each of which is hereby incorporated herein by reference in its entirety and is to be considered as part of this specification. For example, the prosthetic or orthotic system may include both a prosthetic or orthotic ankle and/or a prosthetic or orthotic knee.

Moreover, embodiments of the invention disclosed herein may be performed by one or more software modules. For example, an embodiment of the invention may include a machine loadable software program for a processor for controlling the movement of a device associated with a limb. The software program may include an input module, a filter module, a comparison module, and a control module. The input module may be configured to receive a time series of motion signals. The filter module may be configured to process the time series of motion signals and/or to generate a plurality of filtered signals. The comparison module may be configured to compare the plurality of filtered signals with a plurality of sample signals and configured to generate a gait event selection signal indicative of the movement of a device associated with a limb. The control module may be configured to generate a control signal based at least in part on the gait event selection signal, wherein the control signal is capable of controlling the movement of the device associated with a limb. Furthermore, the software module(s) may include, for example, an AR filter and/or a Kalman filter.

While certain embodiments of the inventions have been described, these embodiments have been presented by way of example only, and are not intended to limit the scope of the disclosure. Indeed, the novel methods and systems described herein may be embodied in a variety of other forms. For example, the foregoing may be applied to the motion-control of joints other than the ankle, such as a knee or a shoulder. Furthermore, various omissions, substitutions and changes in the form of the methods and systems described herein may be made without departing from the spirit of the disclosure. The accompanying claims and their equivalents are intended to cover such forms or modifications as would fall within the scope and spirit of the disclosure.

What is claimed is:

1. A system for analyzing the movement of a device associated with a limb, the system comprising:
   at least one accelerometer configured to generate a time series of motion signals indicative of a movement of a device associated with a limb; and
   a process module in communication with the at least one accelerometer, the process module comprising:
      a filter configured to process the time series of motion signals received from the at least one accelerometer and configured to generate from the time series of motion signals a plurality of filtered signals; and a comparison module configured to compare the plurality of filtered signals with a plurality of sample signals, wherein the comparison module is further configured to identify, based on said comparison, limb-motion events associated with the movement of the device associated with the limb.

2. The system of claim 1, wherein the at least one accelerometer comprises a gyroscope.

3. The system of claim 1, wherein the time series of motion signals comprises at least one of forward, inward and downward linear acceleration signals.

4. The system of claim 1, wherein the filter comprises an autoregressive filter.

5. The system of claim 4, wherein the filter comprises a Kalman filter.

6. The system of claim 1, further comprising a database configured store the plurality of sample signals.

7. The system of claim 1, wherein the process module comprises a machine executable software module.

8. The system of claim 1, wherein the limb is an artificial limb.

9. The system of claim 8, wherein the artificial limb comprises one of a prosthetic device and an orthotic device.

10. A prosthetic device being movable about a joint location and comprising the system of claim 1.

11. The prosthetic device of claim 10, wherein the comparison module is further configured to generate a control signal for adjusting the prosthetic device.

12. The prosthetic device of claim 11, further comprising an actuator configured to control movement of the prosthetic device according to the control signal.

13. The prosthetic device of claim 12, wherein the joint location is an ankle-joint location.

14. The system of claim 8, wherein the at least one accelerometer is attached to the artificial limb.

15. The system of claim 1, wherein the limb-motion events comprise toe-off and heel-strike events.

* * * * *

UNITED STATES PATENT AND TRADEMARK OFFICE
CERTIFICATE OF CORRECTION

| | | |
|---|---|---|
| PATENT NO. | : 7,811,333 B2 | Page 1 of 1 |
| APPLICATION NO. | : 11/315648 | |
| DATED | : October 12, 2010 | |
| INVENTOR(S) | : Helgi Jonsson et al. | |

It is certified that error appears in the above-identified patent and that said Letters Patent is hereby corrected as shown below:

In Column 8, Line 42, after "in" delete "copending".

In Column 16, Line 22, change "as by" to --as--.

In Column 18, Line 16, after "to" insert --1.--.

In Column 18, Line 41, after "to" insert --1.--.

In Column 18, Line 64, after "to" insert --0.--.

Signed and Sealed this
Twenty-sixth Day of April, 2011

David J. Kappos
*Director of the United States Patent and Trademark Office*

UNITED STATES PATENT AND TRADEMARK OFFICE
CERTIFICATE OF CORRECTION

PATENT NO.        : 7,811,333 B2
APPLICATION NO.   : 11/315648
DATED             : October 12, 2010
INVENTOR(S)       : Helgi Jonsson et al.

It is certified that error appears in the above-identified patent and that said Letters Patent is hereby corrected as shown below:

On page 3 under item (56) Other Publications, line 3, change "Rehabilation" to --Rehabilitation--.

Signed and Sealed this
Thirty-first Day of May, 2011

David J. Kappos
*Director of the United States Patent and Trademark Office*